US011926842B2

(12) United States Patent
Gao et al.

(10) Patent No.: US 11,926,842 B2
(45) Date of Patent: Mar. 12, 2024

(54) USE OF INVERTED TERMINAL REPEATS (ITRS) FROM ADENO-ASSOCIATED VIRUS SEROTYPES 8 AND RH.39 IN GENE THERAPY VECTORS

(71) Applicant: University of Massachusetts, Boston, MA (US)

(72) Inventors: Guangping Gao, Westborough, MA (US); Phillip Tai, Worcester, MA (US); Elisabet C. Mandon, Shrewsbury, MA (US); Jianzhong Ai, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 17/590,337

(22) Filed: Feb. 1, 2022

(65) Prior Publication Data

US 2022/0251602 A1 Aug. 11, 2022

Related U.S. Application Data

(60) Provisional application No. 63/144,874, filed on Feb. 2, 2021.

(51) Int. Cl.
*C12N 15/86* (2006.01)
(52) U.S. Cl.
CPC .... *C12N 15/86* (2013.01); *C12N 2750/14143* (2013.01); *C12N 2750/14171* (2013.01)
(58) Field of Classification Search
CPC .......... C12N 15/86; C12N 2750/14143; C12N 2750/14171; C12N 2750/14121; C12N 2750/14122; A61K 48/005
See application file for complete search history.

(56) References Cited

U.S. PATENT DOCUMENTS

| | | | |
|---|---|---|---|
| 7,235,393 B2 | 6/2007 | Gao et al. | |
| 2007/0036760 A1* | 2/2007 | Wilson | A61K 48/00 435/235.1 |
| 2017/0130245 A1 | 5/2017 | Kotin et al. | |
| 2018/0142260 A1* | 5/2018 | Logan | C12N 15/86 |
| 2020/0208176 A1 | 7/2020 | Vandenberghe et al. | |
| 2021/0139933 A1* | 5/2021 | Ling | A61K 48/005 |
| 2021/0163991 A1* | 6/2021 | Gillmeister | C12N 15/86 |
| 2021/0275614 A1* | 9/2021 | Choi | A61K 35/761 |
| 2023/0002786 A1* | 1/2023 | Samulski | C12N 15/86 |

FOREIGN PATENT DOCUMENTS

| | | | |
|---|---|---|---|
| WO | WO 2016/054557 A1 | 4/2016 | |
| WO | WO-2018187552 A1 * | 10/2018 | ........... A61K 35/761 |
| WO | WO 2020/069461 A1 | 4/2020 | |
| WO | WO-2021055760 A1 * | 3/2021 | ......... A61K 48/0058 |

OTHER PUBLICATIONS

Zhou, Xiaoyang, et al. "90. Evaluation of Novel Gene Transfer Vectors Derived from Infectious Molecular Clones of Primate AAVs." Molecular Therapy 9.S1 (2004): S36. (Year: 2004).*
Earley et al., Adeno-Associated Virus Serotype-Specific Inverted Terminal Repeat Sequence Role in Vector Transgene Expression. Hum Gene Ther. Feb. 2020;31(3-4):151-162. doi: 10.1089/hum. 2019.274.
Gao et al., Adeno-associated viruses undergo substantial evolution in primates during natural infections. Proc Natl Acad Sci U S A. May 13, 2003;100(10):6081-6. doi: 10.1073/pnas.0937739100. Epub Apr. 25, 2003.
Gao et al., Clades of Adeno-associated viruses are widely disseminated in human tissues. J Virol. Jun. 2004;78(12):6381-8. doi: 10.1128/JVI.78.12.6381-6388.2004.
Gao et al., Novel adeno-associated viruses from rhesus monkeys as vectors for human gene therapy. Proc Natl Acad Sci U S A. Sep. 3, 2002;99(18):11854-9. doi: 10.1073/pnas.182412299. Epub Aug. 21, 2002.
Xiao et al., Gene therapy vectors based on adeno-associated virus type 1. J Virol. May 1999;73(5):3994-4003. doi: 10.1128/JVI.73.5. 3994-4003.1999.
Xiao et al., Production of high-titer recombinant adeno-associated virus vectors in the absence of helper adenovirus. J Virol. Mar. 1998;72(3):2224-32. doi: 10.1128/JVI.72.3.2224-2232.1998.
Invitation to Pay Additional Fees for Application No. PCT/US2022/ 014776, dated May 9, 2022.
International Search Report and Written Opinion for Application No. PCT/US2022/014776, dated Jul. 5, 2022.
International Preliminary Report on Patentability for Application No. PCT/US2022/014776, dated Aug. 17, 2023.
Mietzsch et al., Comparative Analysis of the Capsid Structures of AAVrh.10, AAVrh.39, and AAV8. J Virol. Feb. 28, 2020;94(6):e01769-19. doi: 10.1128/JVI.01769-19. Print Feb. 28, 2020.

* cited by examiner

*Primary Examiner* — Titilayo Moloye
(74) *Attorney, Agent, or Firm* — Wolf, Greenfield & Sacks, P.C.

(57) ABSTRACT

In some aspects, the disclosure provides recombinant AAV and nucleic acid constructs having novel inverted terminal repeats (ITRs), cap, and/or rep genes. In some aspects, the disclosure relates to gene transfer methods using rAAVs described herein.

24 Claims, 5 Drawing Sheets

Specification includes a Sequence Listing.

SEQUENCE LISTING

```
<160> NUMBER OF SEQ ID NOS: 18

<210> SEQ ID NO 1
<211> LENGTH: 145
<212> TYPE: DNA
<213> ORGANISM: Artificial Sequence
<220> FEATURE:
<223> OTHER INFORMATION: Synthetic

<400> SEQUENCE: 1
ggttacccct agtgatggag ttggccactc cctctatgcg cgctcgctcg ctcggtgggg      60
ccggcagagc agagctctgc cgtctgcgga cctttggtcc gcaggcccca ccgagcgagc     120
gagcgcgcat agagggagtg gccaa                                           145

<210> SEQ ID NO 2
<211> LENGTH: 145
<212> TYPE: DNA
<213> ORGANISM: Artificial sequence
<220> FEATURE:
<223> OTHER INFORMATION: Synthetic

<400> SEQUENCE: 2
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taacc                                           145

<210> SEQ ID NO 3
<211> LENGTH: 145
<212> TYPE: DNA
<213> ORGANISM: Artificial sequence
<220> FEATURE:
<223> OTHER INFORMATION: Synthetic

<400> SEQUENCE: 3
ggttacccct agtgatggag ttggccactc cctctatgcg cgctcgctcg ctcggtgggg      60
ccggctgagc agagctcagc cgtctgcgga cctttggtcc gcaggcccca ccgagcgagc     120
gagcgcgcat agagggagtg gccaa                                           145

<210> SEQ ID NO 4
<211> LENGTH: 145
<212> TYPE: DNA
<213> ORGANISM: Artificial sequence
<220> FEATURE:
<223> OTHER INFORMATION: Synthetic

<400> SEQUENCE: 4
```

```
ttggccactc cctctatgcg cgctcgctcg ctcggtgggg cctgcggacc aaaggtccgc      60
agacggctga gctctgctca gccggccccca ccgagcgagc gagcgcgcat agagggagtg    120
gccaactcca tcactagggg taacc                                           145
```

<210> SEQ ID NO 5
<211> LENGTH: 4715
<212> TYPE: DNA
<213> ORGANISM: Artificial sequence
<220> FEATURE:
<223> OTHER INFORMATION: Synthetic

<400> SEQUENCE: 5

```
ttggccactc cctctatgcg cgctcgctcg ctcggtgggg cctgcggacc aaaggtccgc      60
agacggcaga gctctgctct gccggcccca ccgagcgagc gagcgcgcat agagggagtg    120
gccaactcca tcactagggg taacctccca cgctgccgcg tcagcgctga cgtaaattac    180 gtcataggg  agtggtcctg tattagctgt cacgtgagtg cttttgcggc attttgcgac    240
accacgtggc catttgaggt atatatggcc gagtgagcga gcaggatctc cattttgacc    300
gcgaaatttg aacgagcagc agccatgccg ggcttctacg agatcgtgat caaggtgccg    360
agcgacctgg acgagcacct gccgggcatt tctgactcgt tgtgaactg  ggtggccgag    420 aaggaatggg agctgccccc ggattctgac atggatcgga atctgatcga gcaggcaccc    480
ctgaccgtgg ccgagaagct gcagcgcgac ttcctggtcc aatggcgccg cgtgagtaag    540
gccccggagg ccctcttctt tgttcagttc gagaagggcg agagctactt tcacctgcac    600
gttctggtcg agaccacggg ggtcaagtcc atggtgctag gccgcttcct gagtcagatt    660
cgggagaagc tggtccagac catctaccgc ggggtcgagc ccacgctgcc caactggttc    720
gcggtgacca agacgcgtaa tggcgccggc gggggggaaca aggtggtgga cgagtgctac    780
atccccaact acctcctgcc caagactcag cccgagctgc agtgggcgtg gactaacatg    840
gaggagtata agcgcgtg  cttgaacctg gccgagcgca acggctcgt  ggcgcagcac    900 ctgacccacg tcagccagac gcaggagcag aacaaggaga atctgaaccc caattctgac    960
gcgcccgtga tcaggtcaaa aacctccgcg cgctatatgg agctggtcgg gtggctggtg   1020
gaccggggca tcacctccga gaagcagtgg atccaggagg accaggcctc gtacatctcc   1080
ttcaacgccg cctccaactc gcggtcccag atcaaggccg cgctggacaa tgccggcaag   1140
atcatggcgc tgaccaaaatc cgcgcccgac tacctggtgg ggccctcgct gcccgcggac   1200
attacccaga accgcatcta ccgcatcctc gctctcaacg gctacgaccc tgcctacgcc   1260
ggctccgtct ttctcggctg ggctcagaaa agttcggga  aacgcaacac catctggctg   1320
tttggacccg ccaccaccgg caagaccaac attgcggaag ccatcgccca cgccgtgccc   1380
ttctacggct gcgtcaactg gaccaatgag aactttccct tcaatgattg cgtcgacaag   1440
atggtgatct ggtgggagga gggcaagatg acggccaagg tcgtggagtc cgccaaggcc   1500
attctcggcg gcagcaaggt gcgcgtggac caaaagtgca agtcgtccgc ccagatcgac   1560
cccacccccg tgatcgtcac ctccaacacc aacatgtgcg ccgtgattga cgggaacagc   1620
accaccttcg agcaccagca gcctctccag gaccggatgt ttaagttcga actcacccgc   1680
cgtctggagc acgactttgg caaggtgaca aagcaggaag tcaaagagtt cttccgctgg   1740
gccagtgatc acgtgaccga ggtggcgcat gagttttacg tcagaaaggg cggagccagc   1800
aaaagacccg cccccgatga cgcggataaa agcgagccca gcggggcctg cccctcagtc   1860
```

```
gcggatccat cgacgtcaga cgcggaagga gctccggtgg actttgccga caggtaccaa    1920
aacaaatgtt ctcgtcacgc gggcatgctt cagatgctgt ttccctgcaa acgtgcgag    1980 agaatgaatc agaatttcaa catttgcttc acacacgggg tcagagactg ctcagagtgt    2040
ttccccggcg tgtcagaatc tcaaccggtc gtcagaaaga ggacgtatcg gaaactctgt    2100
gcgattcatc atctgctggg gcgggctccc gagattgctt gctcggcctg cgatctggtc    2160
aacgtggacc tggatgactg tgtttctgag caataaatga cttaaaccag gtatggctgc    2220
cgatggttat cttccagatt ggctcgagga caacctctct gagggcattc gcgagtggtg    2280
ggcgctgaaa cctggagccc cgaagcccaa agccaaccag caaaagcagg acgacggccg    2340
gggtctggtg cttcctggct acaagtacct cggacccttc aacggactcg acaaggggga    2400
gcccgtcaac gcggcggacg cagcggccct cgagcacgac aaggcctacg accagcagct    2460
gcaggcgggt gacaatccgt acctgcggta taaccacgcc gacgccgagt tcaggagcg    2520 tctgcaagaa gatacgtctt ttgggggcaa cctcgggcga gcagtcttcc aggccaagaa    2580
gcgggttctc gaacctctcg gtctggttga ggaaggcgct aagacggctc ctggaaagaa    2640
gagaccggta gagccatcac cccagcgttc tccagactcc tctacgggca tcggcaagaa    2700
aggccaacag cccgccagaa aaagactcaa ttttggtcag actggcgact cagagtcagt    2760
tccagaccct caacctctcg gagaacctcc agcagcgccc tctggtgtgg gacctaatac    2820
aatggctgca ggcggtggcg caccaatggc agacaataac gaaggcgccg acggagtggg    2880
tagttcctcg ggaaattggc attgcgattc cacatggctg ggcgacagag tcatcaccac    2940
cagcacccga acctgggccc tgcccaccta caacaaccac ctctacaagc aaatctccaa    3000
cgggacatcg ggaggagcca ccaacgacaa cacctacttc ggctacagca cccctggg    3060 gtattttgac tttaacagat tccactgcca cttttcacca cgtgactggc agcgactcat    3120
caacaacaac tggggattcc ggcccaagag actcagcttc aagctcttca acatccaggt    3180
caaggaggtc acgcagaatg aaggcaccaa gaccatcgcc aataacctca ccagcaccat    3240
ccaggtgttt acggactcgg agtaccagct gccgtacgtt ctcggctctg cccaccaggg    3300
ctgcctgcct ccgttcccgg cggacgtgtt catgattccc cagtacggct acctaacact    3360
caacaacggt agtcaggccg tgggacgctc ctccttctac tgcctggaat actttccttc    3420
gcagatgctg agaaccggca caacttcca gtttacttac accttcgagg acgtgccttt    3480
ccacagcagc tacgcccaca ccagagctt ggaccggctg atgaatcctc tgattgacca    3540
gtacctgtac tacttgtctc ggactcaaac aacaggaggc acggcaaata cgcagactct    3600
gggcttcagc caaggtgggc ctaatacaat ggccaatcag gcaaagaact ggctgccagg    3660
accctgttac cgccaacaac gcgtctcaac gacaaccggg caaaacaaca atagcaactt    3720
tgcctggact gctgggacca ataccatct gaatggaaga aattcattgg ctaatcctgg    3780
catcgctatg gcaacacaca aagacgacaa ggagcgtttt tttcccagta cgggatcct    3840 gattttggc aaacaaaatg ctgccagaga caatgcggat tacagcgatg tcatgctcac    3900
cagcgaggaa gaaatcaaaa ccactaaccc tgtggctaca gaggaatacg gtatcgtggc    3960
agataacttg cagcagcaaa acacggctcc tcaaattgga actgtcaaca gccaggggca    4020
cttacccggt atggtctggc agaaccggga cgtgtacctg cagggtccca tctgggccaa    4080
gattcctcac acggacggca acttccaccc gtctccgctg atgggcggct ttggcctgaa    4140
acatcctccg cctcagatcc tgatcaagaa cacgcctgta cctgcggatc ctccgaccac    4200
cttcaaccag tcaaagctga actctttcat cacgcaatac agcaccggac aggtcagcgt    4260
```

```
ggaaattgaa tgggagctgc agaaggaaaa cagcaagcgc tggaaccccg agatccagta    4320
cacctccaac tactacaaat ctacaagtgt ggactttgct gttaatacag aaggcgtgta    4380
ctctgaaccc cgccccattg gcacccgtta cctcacccgt aatctgtaat tgcctgttaa    4440
tcaataaacc ggttgattcg tttcagttga actttggcct actgtccttc ttatcttatc    4500
tcgtctccat ggcaactggt taaacattaa ctgcttgggt gcgcttcgcg ataagggact    4560
gacgtcatcg ggttaccccct agtgatggag ttggccactc cctctatgcg cgctcgctcg    4620
ctcggtgggg ccggcagagc agagctctgc cgtctgcgga cctttggtcc gcaggcccca    4680
ccgagcgagc gagcgcgcat agagggagtg gccaa                               4715
```

<210> SEQ ID NO 6
<211> LENGTH: 4725
<212> TYPE: DNA
<213> ORGANISM: Artificial sequence
<220> FEATURE:
<223> OTHER INFORMATION: Synthetic

<400> SEQUENCE: 6

```
ttggccactc cctctatgcg cgctcgctcg ctcggtgggg cctgcggacc aaaggtccgc      60
agacggctga gctctgctca gccggcccca ccgagcgagc gagcgcgcat agagggagtg     120
gccaactcca tcactagggg taaccgcgaa gcgcctccca cgctgccgcg tcagcgctga     180
cgtaaatcac gtcatagggg agtggtcctg tattagctgt cacgtgagtg cttttgcgac     240
agtttgcgac accacgtggt cacagggggt atatatggcc gagtgagcac gcaggatctc     300
cattttgagc gcggaatttg aacgagcagc agccatgccg ggcttctacg agatcgtgat     360
caaggtgccg agcgacctgg acgagcacct gccgggcatt tctgactcgt tcgtgaactg     420
ggtggccgag aaggaatggg agctgccccc ggattctgac atggatcgga atctgatcga     480
gcaggcaccc ctgaccgtgg ccgagaagct gcagcgcgac ttcctggtcg aatggcgccg     540
cgtgagtaag gccccggagg ccctcttctt tgttcagttc gagaaggggg aaagctactt     600
tcacctgcac gttctggtcg agaccacggg ggtcaagtcc atggtgctgg gccgcttcct     660
gagccagatt cgcgaaaagc tcgtgcaacg catctaccgc ggggtcgagc ccacgctgcc     720
caactggttc gcggtgacca agacgcgaaa tggcgccggc gggggaaca aggtggtgga     780
cgagtgctac atccccaact acctcctgcc caagacgcag cccgagctgc agtgggcgtg     840
gactaacatg gaggagtata taagcgcgtg tctgaacctc gcggagcgta acggctcgt     900
ggcgcagcac ctgaccccacg tcagccagac gcaggagcag aacaaggaga atctgaaccc     960
gaattctgac gcgcccgtga tcaggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cctccaactc gcggtcccag atcaaggccg cgctggacaa    1140
tgccggaaag atcatggcgc tgaccaaatc gcgcccgac tacctggtgg gcccgtcctt    1200
acccgcggac attaaggcca accgcatcta ccgcatcctg gagctcaacg gctacgaccc    1260
cgcctacgcc ggctccgtct tcctgggctg ggcgcagaaa aagttcggta acgcaacac    1320
catctggctc ttcgggcccg ccaccaccgg caagaccaac atcgcggaag ccatcgccca    1380
cgccgtgccc ttctacggct gcgtcaactg gaccaatgag aactttccct tcaacgattg    1440
cgtcgacaag atggtgatct ggtgggagga gggcaagatg accgccaagg tcgtggagtc    1500
cgccaaggcc attctgggtg gaagcaaggt gcgcgtggac caaaagtgca agtcatcggc    1560
```

-continued

```
ccagatcgac cccacgcccg tgatcgtcac ctccaacacc aacatgtgcg ccgtgatcga      1620
cgggaacagc accaccttcg agcaccagca gcccctgcag gaccgcatgt tcaagttcga      1680
gctcacccgc cgtctggagc acgactttgg caaggtgacc aagcaggaag tcaaagagtt      1740
cttccgctgg gctcaggatc acgtgactga ggtggcgcat gagttctacg tcagaaaggg      1800
cggagccacc aaaagacccg cccccagtga cgcggatata agcgagccca agcgggcctg      1860
cccctcagtt gcggagccat cgacgtcaga cgcggaagca ccgtggact ttgcggacag       1920 gtaccaaaac aaatgttctc gtcacgcggg catgcttcag atgctgtttc cctgcaagac      1980
atgcgagaga atgaatcaga atttcaacgt ctgcttcacg cacggggtca gagactgctc      2040
agagtgcttc cccggcgcgt cagaatctca acccgtcgtc agaaaaaaga cgtatcagaa      2100
actgtgcgcg attcatcatc tgctggggcg ggcacccgag attgcgtgtt cggcctgcga      2160
tctcgtcaac gtggacttgg atgactgtgt ttctgagcaa taaatgactt aaaccaggta      2220
tggctgctga cggttatctt ccagattggc tcgaggacaa cctctctgag ggcattcgcg      2280
agtggtggga cctgaaacct ggagccccca gcccaaggc caaccagcag aagcaggacg       2340
acggccgggg tctggtgctt cctggctaca agtacctcgg acccttcaac ggactcgaca      2400 aggggggagcc cgtcaacgcg gcggacgcag cggccctcga gcacgacaag gcctacgacc     2460
agcagctcaa agcgggtgac aatccgtacc tgcggtataa ccacgccgac gccgagtttc      2520
aggagcgtct gcaagaagat acgtcttttg ggggcaacct cgggcgagca gtcttccagg      2580
ccaagaagcg ggttctcgaa cctctcggtc tggttgagga agctgctaag acggctcctg      2640
gaaagaagag accggtagaa ccgtcacctc agcgttcccc cgactcctcc acgggcatcg      2700
gcaagaaagg ccagcagccc gctaaaaaga gactgaactt tggtcagact ggcgactcag      2760
agtcagtccc cgaccctcaa ccaatcggag aaccaccagc aggcccctct ggtctgggat      2820
ctggtacaat ggctgcaggc ggtggcgctc caatggcaga caataacgaa ggcgccgacg      2880
gagtgggtag ttcctcagga aattggcatt gcgattccac atggctgggc gacagagtca      2940
tcaccaccag cacccgaacc tgggccctgc ccacctacaa caaccacctc tacaagcaaa      3000
tatccaatgg gacatcggga ggaagcacca acgacaacac ctacttcggc tacagcaccc      3060
cctgggggta ttttgacttc aacagattcc actgccactt ctccaccgt gactggcagc       3120 gactcatcaa caacaactgg ggattccggc aaaaagact cagcttcaag ctcttcaaca       3180
tccaggtcaa ggaggtcacg cagaatgaag gcaccaagac catcgccaat aaccttacca      3240
gcacgattca ggtatttacg gactcggaat accagctgcc gtacgtcctc ggctccgcgc      3300
accagggctg cctgcctccg ttcccggcgg acgtcttcat gattccccag tacggctacc      3360
ttacactgaa caatggaagt caagccgtag gccgttcctc cttctactgc ctggaatatt      3420
ttccatctca aatgctgcga actggaaaca attttgaatt cagctacacc ttcgaggacg      3480
tgcctttcca cagcagctac gcacacagcc agagcttgga ccgactgatg aatcctctca      3540
tcgaccagta cctgtactac ttatccagaa ctcagtccac aggaggaact caaggtaccc      3600
agcaattgtt attttctcaa gctgggcctg caaacatgtc ggctcaggct aagaactggc      3660
tacctggacc ttgctaccgg cagcagcgag tctctacgac actgtcgcaa acaacaacaa      3720
gcaactttgc ttggactggt gccaccaaat atcacctgaa cggaagagac tctttggtaa      3780
atcccggtgt cgccatggca acccacaagg acgacgagga acgcttcttc ccgtcgagtg      3840
gagtcctgat gtttgaaaa cagggtgctg gaagagacaa tgtggactac agcagcgtta      3900
tgctaaccag cgaagaagaa attaaaacca ctaaccctgt agccacagaa caatacggtg      3960
```

-continued

```
tggtggctga caacttgcag caaaccaata cagggcctat tgtgggaaat gtcaacagcc   4020
aaggagcctt acctggcatg gtctggcaga accgagacgt gtacctgcag ggtcccatct   4080
gggccaagat tcctcacacg gacggcaact tccacccttc accgctaatg ggaggatttg   4140
gactgaagca cccacctcct cagatcctga tcaagaacac gccggtacct gcggatcctc   4200
caacaacgtt cagccaggcg aaattggctt ccttcattac gcagtacagc accggacagg   4260
tcagcgtgga aatcgagtgg gagctgcaga aggagaacag caaacgctgg aacccagaga   4320
ttcagtacac ttcaaaactac tacaaatcta caaatgtgga ctttgctgtc aatacagagg   4380
gaacttattc tgagcctcgc cccattggta ctcgttacct cacccgtaat ctgtaattgc   4440
tggttaatca ataaaccgtt tgattcgttt cagttgaact ttggtctccg tgtgcttctt   4500
atcttatctc gtctccatgg caactggtta cacattaact gcttggtgcg cttcgcgatc   4560
ataaatgact tacgtcatcg ggttacccct agtgatggag ttggccactc cctctatgcg   4620
cgctcgctcg ctcggtgggg ccggctgagc agagctcagc cgtctgcgga cctttggtcc   4680
gcaggcccca ccgagcgagc gagcgcgcat agagggagtg gccaa              4725
```

<210> SEQ ID NO 7
<211> LENGTH: 623
<212> TYPE: PRT
<213> ORGANISM: Artificial sequence
<220> FEATURE:
<223> OTHER INFORMATION: Synthetic

<400> SEQUENCE: 7

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220
```

```
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
        260                 265                 270

Ile Met Ala Leu Thr Lys Ser Ala Pro Asp Tyr Leu Val Gly Pro Ser
    275                 280                 285

Leu Pro Ala Asp Ile Thr Gln Asn Arg Ile Tyr Arg Ile Leu Ala Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
        340                 345                 350

Phe Tyr Gly Cys Val Asn Trp Thr Asn Glu Asn Phe Pro Phe Asn Asp
    355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
    435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
            485                 490                 495

Pro Asp Asp Ala Asp Lys Ser Glu Pro Lys Arg Ala Cys Pro Ser Val
        500                 505                 510

Ala Asp Pro Ser Thr Ser Asp Ala Glu Gly Ala Pro Val Asp Phe Ala
    515                 520                 525

Asp Arg Tyr Gln Asn Lys Cys Ser Arg His Ala Gly Met Leu Gln Met
530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Ser Glu Cys Phe Pro Gly Val
            565                 570                 575

Ser Glu Ser Gln Pro Val Val Arg Lys Arg Thr Tyr Arg Lys Leu Cys
        580                 585                 590

Ala Ile His His Leu Leu Gly Arg Ala Pro Glu Ile Ala Cys Ser Ala
    595                 600                 605

Cys Asp Leu Val Asn Val Asp Leu Asp Asp Cys Val Ser Glu Gln
610                 615                 620

<210> SEQ ID NO 8
<211> LENGTH: 537
<212> TYPE: PRT
```

<213> ORGANISM: Artificial sequence
<220> FEATURE:
<223> OTHER INFORMATION: Synthetic

<400> SEQUENCE: 8

| Met | Pro | Gly | Phe | Tyr | Glu | Ile | Val | Ile | Lys | Val | Pro | Ser | Asp | Leu | Asp |
|---|---|---|---|---|---|---|---|---|---|---|---|---|---|---|---|
| 1 | | | | 5 | | | | | 10 | | | | | 15 | |

| Glu | His | Leu | Pro | Gly | Ile | Ser | Asp | Ser | Phe | Val | Asn | Trp | Val | Ala | Glu |
| | | | 20 | | | | | 25 | | | | | 30 | | |

| Lys | Glu | Trp | Glu | Leu | Pro | Pro | Asp | Ser | Asp | Met | Asp | Arg | Asn | Leu | Ile |
| | | 35 | | | | | 40 | | | | 45 | | | | |

| Glu | Gln | Ala | Pro | Leu | Thr | Val | Ala | Glu | Lys | Leu | Gln | Arg | Asp | Phe | Leu |
| 50 | | | | | 55 | | | | | 60 | | | | | |

| Val | Gln | Trp | Arg | Arg | Val | Ser | Lys | Ala | Pro | Glu | Ala | Leu | Phe | Phe | Val |
| 65 | | | | 70 | | | | | 75 | | | | | 80 | |

| Gln | Phe | Glu | Lys | Gly | Glu | Ser | Tyr | Phe | His | Leu | His | Val | Leu | Val | Glu |
| | | | | 85 | | | | | 90 | | | | | 95 | |

| Thr | Thr | Gly | Val | Lys | Ser | Met | Val | Leu | Gly | Arg | Phe | Leu | Ser | Gln | Ile |
| | | | | 100 | | | | | 105 | | | | | 110 | |

| Arg | Glu | Lys | Leu | Val | Gln | Thr | Ile | Tyr | Arg | Gly | Val | Glu | Pro | Thr | Leu |
| | | | 115 | | | | | 120 | | | | | 125 | | |

| Pro | Asn | Trp | Phe | Ala | Val | Thr | Lys | Thr | Arg | Asn | Gly | Ala | Gly | Gly | Gly |
| | 130 | | | | | 135 | | | | | 140 | | | | |

| Asn | Lys | Val | Val | Asp | Glu | Cys | Tyr | Ile | Pro | Asn | Tyr | Leu | Leu | Pro | Lys |
| 145 | | | | | 150 | | | | | 155 | | | | | 160 |

| Thr | Gln | Pro | Glu | Leu | Gln | Trp | Ala | Trp | Thr | Asn | Met | Glu | Glu | Tyr | Ile |
| | | | | 165 | | | | | 170 | | | | | 175 | |

| Ser | Ala | Cys | Leu | Asn | Leu | Ala | Glu | Arg | Lys | Arg | Leu | Val | Ala | Gln | His |
| | | | 180 | | | | | 185 | | | | | 190 | | |

| Leu | Thr | His | Val | Ser | Gln | Thr | Gln | Glu | Gln | Asn | Lys | Glu | Asn | Leu | Asn |
| | | 195 | | | | | 200 | | | | | 205 | | | |

| Pro | Asn | Ser | Asp | Ala | Pro | Val | Ile | Arg | Ser | Lys | Thr | Ser | Ala | Arg | Tyr |
| | 210 | | | | | 215 | | | | | 220 | | | | |

| Met | Glu | Leu | Val | Gly | Trp | Leu | Val | Asp | Arg | Gly | Ile | Thr | Ser | Glu | Lys |
| 225 | | | | | 230 | | | | | 235 | | | | | 240 |

| Gln | Trp | Ile | Gln | Glu | Asp | Gln | Ala | Ser | Tyr | Ile | Ser | Phe | Asn | Ala | Ala |
| | | | | 245 | | | | | 250 | | | | | 255 | |

| Ser | Asn | Ser | Arg | Ser | Gln | Ile | Lys | Ala | Ala | Leu | Asp | Asn | Ala | Gly | Lys |
| | | | 260 | | | | | 265 | | | | | 270 | | |

| Ile | Met | Ala | Leu | Thr | Lys | Ser | Ala | Pro | Asp | Tyr | Leu | Val | Gly | Pro | Ser |
| | | 275 | | | | | 280 | | | | | 285 | | | |

| Leu | Pro | Ala | Asp | Ile | Thr | Gln | Asn | Arg | Ile | Tyr | Arg | Ile | Leu | Ala | Leu |
| | 290 | | | | | 295 | | | | | 300 | | | | |

| Asn | Gly | Tyr | Asp | Pro | Ala | Tyr | Ala | Gly | Ser | Val | Phe | Leu | Gly | Trp | Ala |
| 305 | | | | | 310 | | | | | 315 | | | | | 320 |

| Gln | Lys | Lys | Phe | Gly | Lys | Arg | Asn | Thr | Ile | Trp | Leu | Phe | Gly | Pro | Ala |
| | | | | 325 | | | | | 330 | | | | | 335 | |

| Thr | Thr | Gly | Lys | Thr | Asn | Ile | Ala | Glu | Ala | Ile | Ala | His | Ala | Val | Pro |
| | | | 340 | | | | | 345 | | | | | 350 | | |

| Phe | Tyr | Gly | Cys | Val | Asn | Trp | Thr | Asn | Glu | Asn | Phe | Pro | Phe | Asn | Asp |
| | | 355 | | | | | 360 | | | | | 365 | | | |

| Cys | Val | Asp | Lys | Met | Val | Ile | Trp | Trp | Glu | Glu | Gly | Lys | Met | Thr | Ala |
| | 370 | | | | | 375 | | | | | 380 | | | | |

| Lys | Val | Val | Glu | Ser | Ala | Lys | Ala | Ile | Leu | Gly | Gly | Ser | Lys | Val | Arg |

```
                385                 390                 395                 400
Val Asp Gln Lys Cys Lys Ser Ser Ala Gln Ile Asp Pro Thr Pro Val
                    405                 410                 415

Ile Val Thr Ser Asn Thr Asn Met Cys Ala Val Ile Asp Gly Asn Ser
                    420                 425                 430

Thr Thr Phe Glu His Gln Gln Pro Leu Gln Asp Arg Met Phe Lys Phe
                    435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                    485                 490                 495

Pro Asp Asp Ala Asp Lys Ser Glu Pro Lys Arg Ala Cys Pro Ser Val
                    500                 505                 510

Ala Asp Pro Ser Thr Ser Asp Ala Glu Gly Ala Pro Val Asp Phe Ala
                    515                 520                 525

Asp Arg Leu Ala Arg Gly His Ser Leu
            530                 535

<210> SEQ ID NO 9
<211> LENGTH: 399
<212> TYPE: PRT
<213> ORGANISM: Artificial sequence
<220> FEATURE:
<223> OTHER INFORMATION: Synthetic

<400> SEQUENCE: 9

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
            35                  40                  45

Ile Met Ala Leu Thr Lys Ser Ala Pro Asp Tyr Leu Val Gly Pro Ser
50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
                100                 105                 110

Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
        130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
                    180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
```

```
                210                 215                 220
Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Ala Ser Lys Arg Pro Ala
                260                 265                 270

Pro Asp Asp Ala Asp Lys Ser Glu Pro Lys Arg Ala Cys Pro Ser Val
                275                 280                 285

Ala Asp Pro Ser Thr Ser Asp Ala Glu Gly Ala Pro Val Asp Phe Ala
                290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Ser Glu Cys Phe Pro Gly Val
                340                 345                 350

Ser Glu Ser Gln Pro Val Val Arg Lys Arg Thr Tyr Arg Lys Leu Cys
                355                 360                 365

Ala Ile His His Leu Leu Gly Arg Ala Pro Glu Ile Ala Cys Ser Ala
                370                 375                 380

Cys Asp Leu Val Asn Val Asp Leu Asp Asp Cys Val Ser Glu Gln
385                 390                 395

<210> SEQ ID NO 10
<211> LENGTH: 313
<212> TYPE: PRT
<213> ORGANISM: Artificial sequence
<220> FEATURE:
<223> OTHER INFORMATION: Synthetic

<400> SEQUENCE: 10

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
                35                  40                  45

Ile Met Ala Leu Thr Lys Ser Ala Pro Asp Tyr Leu Val Gly Pro Ser
50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
                100                 105                 110

Thr Thr Gly Lys Thr Asn Ile Ala Glu Ala Ile Ala His Ala Val Pro
                115                 120                 125

Phe Tyr Gly Cys Val Asn Trp Thr Asn Glu Asn Phe Pro Phe Asn Asp
                130                 135                 140

Cys Val Asp Lys Met Val Ile Trp Trp Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
```

```
                    180                 185                 190
Ile Val Thr Ser Asn Thr Asn Met Cys Ala Val Ile Asp Gly Asn Ser
                195                 200                 205
Thr Thr Phe Glu His Gln Gln Pro Leu Gln Asp Arg Met Phe Lys Phe
    210                 215                 220
Glu Leu Thr Arg Arg Leu Glu His Asp Phe Gly Lys Val Thr Lys Gln
225                 230                 235                 240
Glu Val Lys Glu Phe Phe Arg Trp Ala Ser Asp His Val Thr Glu Val
                245                 250                 255
Ala His Glu Phe Tyr Val Arg Lys Gly Gly Ala Ser Lys Arg Pro Ala
            260                 265                 270
Pro Asp Asp Ala Asp Lys Ser Glu Pro Lys Arg Ala Cys Pro Ser Val
        275                 280                 285
Ala Asp Pro Ser Thr Ser Asp Ala Glu Gly Ala Pro Val Asp Phe Ala
    290                 295                 300
Asp Arg Leu Ala Arg Gly His Ser Leu
305                 310

<210> SEQ ID NO 11
<211> LENGTH: 622
<212> TYPE: PRT
<213> ORGANISM: Artificial sequence
<220> FEATURE:
<223> OTHER INFORMATION: Synthetic

<400> SEQUENCE: 11

Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
                20                  25                  30
Lys Glu Trp Glu Leu Pro Pro Asp Ser Asp Met Asp Arg Asn Leu Ile
            35                  40                  45
Glu Gln Ala Pro Leu Thr Val Ala Glu Lys Leu Gln Arg Asp Phe Leu
        50                  55                  60
Val Glu Trp Arg Arg Val Ser Lys Ala Pro Glu Ala Leu Phe Phe Val
65                  70                  75                  80
Gln Phe Glu Lys Gly Glu Ser Tyr Phe His Leu His Val Leu Val Glu
                85                  90                  95
Thr Thr Gly Val Lys Ser Met Val Leu Gly Arg Phe Leu Ser Gln Ile
                100                 105                 110
Arg Glu Lys Leu Val Gln Arg Ile Tyr Arg Gly Val Glu Pro Thr Leu
            115                 120                 125
Pro Asn Trp Phe Ala Val Thr Lys Thr Arg Asn Gly Ala Gly Gly Gly
        130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Glu Tyr Ile
                165                 170                 175
Ser Ala Cys Leu Asn Leu Ala Glu Arg Lys Arg Leu Val Ala Gln His
                180                 185                 190
Leu Thr His Val Ser Gln Thr Gln Glu Gln Asn Lys Glu Asn Leu Asn
            195                 200                 205
Pro Asn Ser Asp Ala Pro Val Ile Arg Ser Lys Thr Ser Ala Arg Tyr
        210                 215                 220
Met Glu Leu Val Gly Trp Leu Val Asp Arg Gly Ile Thr Ser Glu Lys
```

```
            225                 230                 235                 240
        Gln Trp Ile Gln Glu Asp Gln Ala Ser Tyr Ile Ser Phe Asn Ala Ala
                        245                 250                 255
        Ser Asn Ser Arg Ser Gln Ile Lys Ala Ala Leu Asp Asn Ala Gly Lys
                        260                 265                 270
        Ile Met Ala Leu Thr Lys Ser Ala Pro Asp Tyr Leu Val Gly Pro Ser
                        275                 280                 285
        Leu Pro Ala Asp Ile Lys Ala Asn Arg Ile Tyr Arg Ile Leu Glu Leu
                        290                 295                 300
        Asn Gly Tyr Asp Pro Ala Tyr Ala Gly Ser Val Phe Leu Gly Trp Ala
        305                 310                 315                 320
        Gln Lys Lys Phe Gly Lys Arg Asn Thr Ile Trp Leu Phe Gly Pro Ala
                        325                 330                 335
        Thr Thr Gly Lys Thr Asn Ile Ala Glu Ala Ile Ala His Ala Val Pro
                        340                 345                 350
        Phe Tyr Gly Cys Val Asn Trp Thr Asn Glu Asn Phe Pro Phe Asn Asp
                        355                 360                 365
        Cys Val Asp Lys Met Val Ile Trp Trp Glu Glu Gly Lys Met Thr Ala
                        370                 375                 380
        Lys Val Val Glu Ser Ala Lys Ala Ile Leu Gly Gly Ser Lys Val Arg
        385                 390                 395                 400
        Val Asp Gln Lys Cys Lys Ser Ser Ala Gln Ile Asp Pro Thr Pro Val
                        405                 410                 415
        Ile Val Thr Ser Asn Thr Asn Met Cys Ala Val Ile Asp Gly Asn Ser
                        420                 425                 430
        Thr Thr Phe Glu His Gln Gln Pro Leu Gln Asp Arg Met Phe Lys Phe
                        435                 440                 445
        Glu Leu Thr Arg Arg Leu Glu His Asp Phe Gly Lys Val Thr Lys Gln
                        450                 455                 460
        Glu Val Lys Glu Phe Phe Arg Trp Ala Gln Asp His Val Thr Glu Val
        465                 470                 475                 480
        Ala His Glu Phe Tyr Val Arg Lys Gly Gly Ala Thr Lys Arg Pro Ala
                        485                 490                 495
        Pro Ser Asp Ala Asp Ile Ser Glu Pro Lys Arg Ala Cys Pro Ser Val
                        500                 505                 510
        Ala Glu Pro Ser Thr Ser Asp Ala Glu Ala Pro Val Asp Phe Ala Asp
                        515                 520                 525
        Arg Tyr Gln Asn Lys Cys Ser Arg His Ala Gly Met Leu Gln Met Leu
        530                 535                 540
        Phe Pro Cys Lys Thr Cys Glu Arg Met Asn Gln Asn Phe Asn Val Cys
        545                 550                 555                 560
        Phe Thr His Gly Val Arg Asp Cys Ser Glu Cys Phe Pro Gly Ala Ser
                        565                 570                 575
        Glu Ser Gln Pro Val Val Arg Lys Lys Thr Tyr Gln Lys Leu Cys Ala
                        580                 585                 590
        Ile His His Leu Leu Gly Arg Ala Pro Glu Ile Ala Cys Ser Ala Cys
                        595                 600                 605
        Asp Leu Val Asn Val Asp Leu Asp Asp Cys Val Ser Glu Gln
            610                 615                 620

<210> SEQ ID NO 12
<211> LENGTH: 536
<212> TYPE: PRT
<213> ORGANISM: Artificial sequence
```

<220> FEATURE:
<223> OTHER INFORMATION: Synthetic

<400> SEQUENCE: 12

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Arg Ile Tyr Arg Gly Val Glu Pro Thr Leu
        115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Ala Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

```
Val Asp Gln Lys Cys Lys Ser Ser Ala Gln Ile Asp Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Thr Lys Arg Pro Ala
                485                 490                 495

Pro Ser Asp Ala Asp Ile Ser Glu Pro Lys Arg Ala Cys Pro Ser Val
            500                 505                 510

Ala Glu Pro Ser Thr Ser Asp Ala Glu Ala Pro Val Asp Phe Ala Asp
        515                 520                 525

Arg Leu Ala Arg Gly His Ser Leu
    530                 535

<210> SEQ ID NO 13
<211> LENGTH: 398
<212> TYPE: PRT
<213> ORGANISM: Artificial sequence
<220> FEATURE:
<223> OTHER INFORMATION: Synthetic

<400> SEQUENCE: 13

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Lys Ala Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220
```

```
Glu Leu Thr Arg Arg Leu His Asp Phe Gly Lys Val Thr Lys Gln
225                 230                 235                 240

Glu Val Lys Glu Phe Phe Arg Trp Ala Gln Asp His Val Thr Glu Val
            245                 250                 255

Ala His Glu Phe Tyr Val Arg Lys Gly Gly Ala Thr Lys Arg Pro Ala
                260                 265                 270

Pro Ser Asp Ala Asp Ile Ser Glu Pro Lys Arg Ala Cys Pro Ser Val
        275                 280                 285

Ala Glu Pro Ser Thr Ser Asp Ala Glu Ala Pro Val Asp Phe Ala Asp
        290                 295                 300

Arg Tyr Gln Asn Lys Cys Ser Arg His Ala Gly Met Leu Gln Met Leu
305                 310                 315                 320

Phe Pro Cys Lys Thr Cys Glu Arg Met Asn Gln Asn Phe Asn Val Cys
                325                 330                 335

Phe Thr His Gly Val Arg Asp Cys Ser Glu Cys Phe Pro Gly Ala Ser
                340                 345                 350

Glu Ser Gln Pro Val Val Arg Lys Lys Thr Tyr Gln Lys Leu Cys Ala
        355                 360                 365

Ile His His Leu Leu Gly Arg Ala Pro Glu Ile Ala Cys Ser Ala Cys
370                 375                 380

Asp Leu Val Asn Val Asp Leu Asp Asp Cys Val Ser Glu Gln
385                 390                 395
```

<210> SEQ ID NO 14
<211> LENGTH: 312
<212> TYPE: PRT
<213> ORGANISM: Artificial sequence
<220> FEATURE:
<223> OTHER INFORMATION: Synthetic

<400> SEQUENCE: 14

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Lys Ala Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190
```

```
Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Ala Thr Lys Arg Pro Ala
                260                 265                 270

Pro Ser Asp Ala Asp Ile Ser Glu Pro Lys Arg Ala Cys Pro Ser Val
                275                 280                 285

Ala Glu Pro Ser Thr Ser Asp Ala Glu Ala Pro Val Asp Phe Ala Asp
                290                 295                 300

Arg Leu Ala Arg Gly His Ser Leu
305                 310

<210> SEQ ID NO 15
<211> LENGTH: 738
<212> TYPE: PRT
<213> ORGANISM: Artificial sequence
<220> FEATURE:
<223> OTHER INFORMATION: Synthetic

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Gly Val Gly Pro Asn Thr Met Ala Ala Gly Gly
                195                 200                 205

Gly Ala Pro Met Ala Asp Asn Asn Glu Gly Ala Asp Gly Val Gly Ser
                210                 215                 220

Ser Ser Gly Asn Trp His Cys Asp Ser Thr Trp Leu Gly Asp Arg Val
225                 230                 235                 240
```

```
Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Lys Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655
```

```
Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 16
<211> LENGTH: 738
<212> TYPE: PRT
<213> ORGANISM: Artificial sequence
<220> FEATURE:
<223> OTHER INFORMATION: Synthetic

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
```

-continued

```
                275                 280                 285
Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
                450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700
```

```
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 17
<211> LENGTH: 145
<212> TYPE: DNA
<213> ORGANISM: Artificial sequence
<220> FEATURE:
<223> OTHER INFORMATION: Synthetic

<400> SEQUENCE: 17
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcct                                           145

<210> SEQ ID NO 18
<211> LENGTH: 12
<212> TYPE: DNA
<213> ORGANISM: Artificial sequence
<220> FEATURE:
<223> OTHER INFORMATION: Synthetic

<400> SEQUENCE: 18
gctcgctcgc tc                                                          12
```

US 11,926,842 B2

USE OF INVERTED TERMINAL REPEATS (ITRS) FROM ADENO-ASSOCIATED VIRUS SEROTYPES 8 AND RH.39 IN GENE THERAPY VECTORS

RELATED APPLICATIONS

This application claims the benefit under 35 U.S.C. 119(e) of the filing date of U.S. provisional application Ser. No. 63/144,874, filed Feb. 2, 2021, the entire contents of which are incorporated herein by reference.

FEDERALLY SPONSORED RESEARCH

This invention was made with government support under NS076991, HL131471, HD080642, AI121135, HL147367, and W81XWH-17-1-0212 awarded by the National Institutes of Health and the Department of Defense. The government has certain rights in the invention.

BACKGROUND OF INVENTION

Recombinant adeno-associated viruses (rAAVs) are capable of driving stable and sustained transgene expression in target tissues without notable toxicity and host immunogenicity. Approximately 94% of the genomic information within an AAV is replaced by a transgene of interest during preparation and design of an rAAV vector. The remaining 6% of the AAV genome, which typically includes two inverted terminal repeat (ITR) sequences that flank the AAV genome, are beneficial for replication and packaging during AAV production; and in providing stability and persistence when the rAAV vector is delivered to a host cell or subject. To date, several ITRs from different AAV serotypes have been described. Nonetheless, there is an increasing need to identify additional ITRs to improve the process of production and manufacturing, and the efficacy of AAV-based gene therapy.

SUMMARY OF INVENTION

Aspects of the disclosure relate to isolated nucleic acid sequences encoding novel adeno-associated virus (AAV) components. The disclosure is based, in part, on novel configurations of AAV inverted terminal repeat (ITR) sequences and rAAV vectors comprising the same. In some embodiments, rAAV vectors described herein are surprisingly packaged into recombinant AAV (rAAV) particles, for example in a mammalian cell or insect cell production system. In some embodiments, rAAV vectors described herein are useful for delivering one or more transgenes to a cell or subject.

Accordingly, in some aspects, the disclosure provide a recombinant adeno-associated viral (rAAV) vector comprising a transgene flanked by inverted terminal repeats (ITRs), wherein a first ITR is an AAV8 ITR and a second ITR is an AAVrh.39 ITR.

In some embodiments, the first ITR is an AAV8 5' ITR and the second ITR is an AAVrh.39 3' ITR. In some embodiments, the first ITR comprises a nucleic acid sequence of SEQ ID NO: 2. In some embodiments, the second ITR comprises a nucleic acid sequence of SEQ ID NO: 3.

In some embodiments, the first ITR is an AAV8 3' ITR and the second ITR is an AAVrh.39 5' ITR. In some embodiments, the first ITR comprises a nucleic acid sequence of SEQ ID NO: 1. In some embodiments, the second ITR comprises a nucleic acid sequence of SEQ ID NO: 4.

In some aspects, the disclosure provides a recombinant adeno-associated viral (rAAV) vector comprising a transgene flanked by inverted terminal repeats (ITRs), wherein a first ITR comprises SEQ ID NO: 1. In some embodiments, the rAAV vector comprises a second ITR that comprises SEQ ID NO: 2.

In some aspects, the disclosure provides a recombinant adeno-associated viral (rAAV) vector comprising a transgene flanked by inverted terminal repeats (ITRs), wherein a first ITR comprises SEQ ID NO: 2. In some embodiments, the rAAV comprises a second ITR comprising SEQ ID NO: 1.

In some aspects, the disclosure provides a recombinant adeno-associated viral (rAAV) vector comprising a transgene flanked by inverted terminal repeats (ITRs), wherein a first ITR comprises SEQ ID NO: 3. In some embodiments, the rAAV vector comprises a second ITR that comprises SEQ ID NO: 4.

In some aspects, the disclosure provides a recombinant adeno-associated viral (rAAV) vector comprising a transgene flanked by inverted terminal repeats (ITRs), wherein a first ITR comprises SEQ ID NO: 3. In some embodiments, the rAAV vector comprises a second ITR that comprises SEQ ID NO: 4.

In some embodiments, a transgene encodes a protein or an inhibitory nucleic acid. In some embodiments, the inhibitory nucleic acid is a dsRNA, siRNA, shRNA, miRNA, artificial miRNA (amiRNA), or antisense oligonucleotide.

In some embodiments, an rAAV vector comprises a promoter operably linked to the transgene. In some embodiments, the promoter is a tissue specific promoter, inducible promoter, or constitutive promoter. In some embodiments, a tissue specific promoter is a liver-specific thyroxin binding globulin (TBG) promoter, an insulin promoter, a glucagon promoter, a somatostatin promoter, mucin-2 promoter, a pancreatic polypeptide (PPY) promoter, a synapsin-1 (Syn) promoter, a retinoschisin promoter, a K12 promoter, a CC10 promoter, a surfactant protein C (SP-C) promoter, a PRC1 promoter, a RRM2 promoter, uroplakin 2 (UPII) promoter, or a lactoferrin promoter. In some embodiments, a promoter is a cytomegalovirus (CMV) promoter, a CMV early enhancer/chicken β actin (CB6) promoter, or a T7 promoter.

In some aspects, the disclosure provides a host cell comprising an rAAV vector as described herein. In some embodiments, a host cell further comprises a Rep protein having the amino acid sequence set forth in any one of SEQ ID NOs: 7-14. In some embodiments, a host cell comprises a Cap protein having the amino acid sequence of SEQ ID NO: 15 or 16. In some embodiments, the host cell is a HEK293 cell or is derived from a HEK293 cell.

In some embodiments, the disclosure provides a nucleic acid comprising two inverted terminal repeats (ITRs), a rep gene, and a cap gene, wherein the rep gene encodes the amino acid sequence set forth in any one of SEQ ID NOs: 7-14. In some embodiments, the cap gene encodes the amino acid sequence set forth in SEQ ID NO: 15 or 16.

In some aspects, the disclosure provides a pseudotyped AAV comprising (i) an AAV8 3' inverted terminal repeat (ITR) comprising SEQ ID NO: 1; and (ii) a capsid protein of a non-AAV8 AAV serotype.

In some embodiments, the pseudotyped AAV further comprises an AAV8 5' ITR comprising SEQ ID NO: 2. In some embodiments, the pseudotyped AAV further comprises an AAVrh.39 5' ITR comprising SEQ ID NO: 4.

In some embodiments, the disclosure provides a pseudotyped AAV comprising (i) an AAV8 5' inverted terminal repeat (ITR) comprising SEQ ID NO: 2; and (ii) a capsid protein of a non-AAV8 AAV serotype. In some embodiments, the pseudotyped AAV further comprises an AAV8 3' ITR comprising SEQ ID NO: 1. In some embodiments, the pseudotyped AAV further comprises an AAVrh.39 3' ITR comprising SEQ ID NO: 3.

In some embodiments, the disclosure provides a pseudotyped AAV comprising (i) an AAVrh.39 3' inverted terminal repeat (ITR) comprising SEQ ID NO: 3; and (ii) a capsid protein of a non-AAVrh.39 AAV serotype. In some embodiments, the pseudotyped AAV further comprises an AAVrh.39 5' ITR comprising SEQ ID NO: 4. In some embodiments, the pseudotyped AAV further comprises an AAV8 5' ITR comprising SEQ ID NO: 2.

In some aspects, the disclosure provides a pseudotyped AAV comprising (i) an AAVrh.39 5' inverted terminal repeat (ITR) comprising SEQ ID NO: 4; and (ii) a capsid protein of a non-AAVrh.39 AAV serotype. In some embodiments, the pseudotyped AAV further comprises an AAVrh.39 3' ITR comprising SEQ ID NO: 3. In some embodiments, the pseudotyped AAV further comprises an AAV8 3' ITR comprising SEQ ID NO: 1.

In some embodiments, a pseudotyped AAV comprises a non-AAV8 AAV serotype selected from AAV1, AAV2, AAV3B, AAV9, AAVrh.8, AAVrh.10, and AAVrh.39. In some embodiments, a pseudotyped AAV comprises a non-AAVrh.39 AAV serotype selected from AAV1, AAV2, AAV3B, AAV8, AAV9, AAVrh.8, and AAVrh.10.

In some embodiments, a pseudotyped AAV further comprises a transgene.

In some aspects, the disclosure provides a recombinant adeno-associated viral (rAAV) vector comprising a transgene flanked by inverted terminal repeats (ITRs), wherein a first ITR is an AAV2 ITR and a second ITR is an AAVrh.39 ITR or an AAV8 ITR.

In some embodiments, the first ITR comprises the nucleic acid sequence set forth in SEQ ID NO: 17. In some embodiments, the second ITR comprises the nucleic acid sequence set forth in any one of SEQ ID NOs: 1-4.

In some embodiments, the transgene encodes a therapeutic protein, one or more inhibitory nucleic acids, or a combination thereof.

In some embodiments, an rAAV vector further comprises one or more miRNA binding sites.

In some embodiments, the transgene comprises a promoter operably linked to a nucleic acid sequence encoding the therapeutic protein.

In some aspects, the disclosure provides a recombinant adeno-associated virus (rAAV) comprising: an rAAV vector of the disclosure; and an AAV capsid protein, optionally wherein the AAV capsid protein is not of the same serotype as any of the ITRs of the rAAV.

In some aspects, the disclosure provides a recombinant adeno-associated virus (rAAV) comprising (i) an AAV8 3' inverted terminal repeat (ITR) comprising SEQ ID NO: 1; (ii) an AAVrh.39 5' ITR comprising SEQ ID NO: 4 and (ii) an AAV8 capsid protein.

In some aspects, the disclosure provides a recombinant adeno-associated virus (rAAV) comprising (i) an AAV8 3' inverted terminal repeat (ITR) comprising SEQ ID NO: 1; (ii) an AAVrh.39 5' ITR comprising SEQ ID NO: 4 and (ii) an AAVrh.39 capsid protein.

In some aspects, the disclosure provides a recombinant adeno-associated virus (rAAV) comprising (i) an AAV8 5' inverted terminal repeat (ITR) comprising SEQ ID NO: 2; (ii) an AAVrh.39 3' ITR comprising SEQ ID NO: 3; and (iii) an AAV8 capsid protein.

In some aspects, the disclosure provides a recombinant adeno-associated virus (rAAV) comprising (i) an AAV8 5' inverted terminal repeat (ITR) comprising SEQ ID NO: 2; (ii) an AAVrh.39 3' ITR comprising SEQ ID NO: 3; and (iii) an AAVrh.39 capsid protein.

In some aspects, the disclosure provides a method for delivering a transgene to a cell or subject, the method comprising administering to the cell or subject an rAAV vector of the disclosure or an rAAV of the disclosure.

BRIEF DESCRIPTION OF DRAWINGS

FIG. 1A shows a depiction of an rAAV vector genome comprising a transgene operably linked to a promoter and flanked by a 5' ITR and a 3' ITR. FIG. 1B shows a depiction of the sequence and structure of the AAV8 3' ITR (SEQ ID NO: 1) of the disclosure. Rep binding elements (RBE) and a terminal resolution site (TRS) are highlighted. FIG. 1C shows a depiction of the sequence and structure of the AAVrh.39 3' ITR (SEQ ID NO: 3) of the disclosure. Rep binding elements (RBE) and a terminal resolution site (TRS) are highlighted.

FIG. 3A provides a graph showing protein expression of eGFP in liver of mice treated with rAAVs comprising hybrid ITR sequences of the disclosure. FIG. 3B provides a graph showing vector copies of rAAV in liver of mice treated with rAAVs comprising hybrid ITR sequences of the disclosure. FIG. 3C provides graphs showing gene expression of eGFP in liver of mice treated with rAAVs comprising hybrid ITR sequences of the disclosure.

DETAILED DESCRIPTION OF INVENTION

Figure 1A:
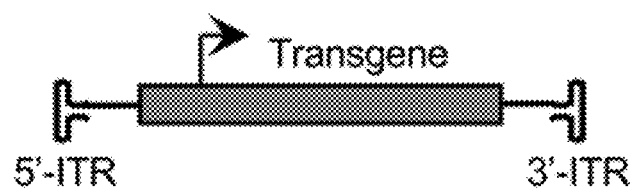
FIGS. 1A-1C depict embodiments of rAAV vector constructs and sequences of the disclosure.
Figure 1B:
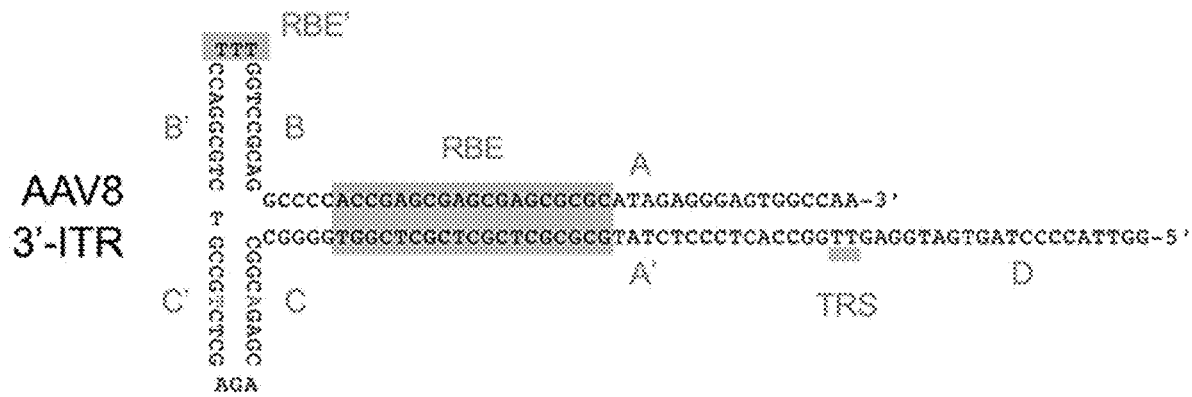
Figure 1C:
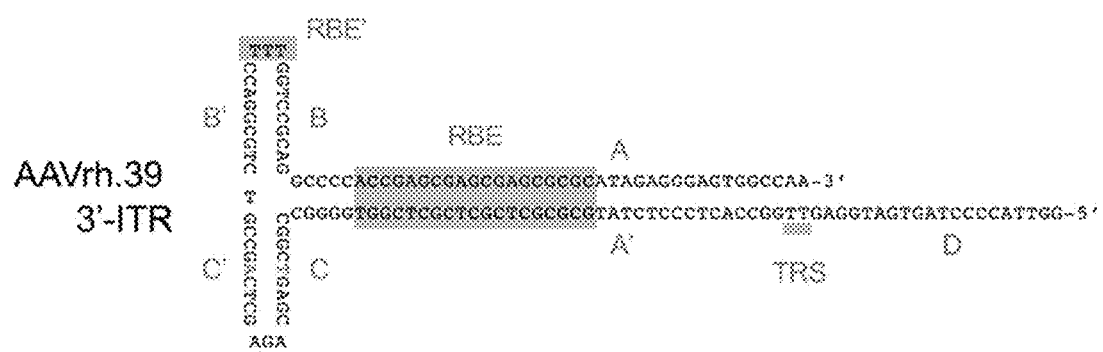

Gene delivery in laboratory and clinical settings has been achieved using vectors derived from adeno-associated viruses (AAVs). Current recombinant AAV (rAAV) vectors have approximately 94% of the AAV genome replaced with a expression cassette comprising a transgene. The remaining 6% of the viral genome is generally required for replication and packaging during production; and stability and persistence when the vector is delivered to the host cell. These viral components include one or two inverted terminal repeat (ITR) sequences that are generally 145-nucleotides in length, that flank the ends of the vector genome. The ITR structure forms a T-shaped hairpin. Engineering of the ITR structure through the introduction of mutations have enhanced the outcomes of the different steps in the viral life cycle. For example, changes at the terminal resolution site (TRS), which is required for viral replication, have been used to generate self-complementary AAV vectors (scAAVs). In the clinical context, importantly, ITR(s) are the only viral elements that remain in gene therapy vectors. These ITR sequences are directly linked with AAV genome integration and episomal persistence by circularization and concatemer formation of the vector genome following in vivo delivery. It is also thought that ITRs interact with host proteins and trigger anti-viral and DNA damage-response pathways. The ITRs are beneficial for the stability of AAV vectors, in part because they determine post-entry processing and persistence of the vector. Different ITR sequences (e.g., including the ITRs of the disclosure, e.g., SEQ ID NOs: 1-4) and/or different combinations of ITR sequences display distinctive patterns of vector genome metabolization, which indicates that varying ITR sequences can be manipulated to modulate vector stability, persistence, and safety.

Described herein are novel inverted terminal repeat (ITR) sequences identified as belonging to AAV8 and AAVrh.39 serotypes and the application of said ITR sequences in AAV compositions and vectors. In some embodiments, the AAV8 ITR sequence is a 3' ITR sequence having a nucleic acid sequence as set forth in SEQ ID NO: 1. In some embodiments, the AAV8 ITR sequence is a 5' ITR sequence having a nucleic acid sequence as set forth in SEQ ID NO: 2. In some embodiments, the AAVrh.39 ITR sequence is a 3' ITR sequence having a nucleic acid sequence as set forth in SEQ ID NO: 3. In some embodiments, the AAVrh.39 ITR sequence is a 5' ITR sequence having a nucleic acid sequence as set forth in SEQ ID NO: 4. In some embodiments, the AAV8 ITR sequences are an element of an AAV8 genome (e.g., an AAV8 genome having a nucleic acid sequence as set forth in SEQ ID NO: 5). In some embodiments, the AAVrh.39 ITR sequences are an element of an AAVrh.39 genome (e.g., an AAVrh.39 genome having a nucleic acid sequence as set forth in SEQ ID NO: 6).

In some embodiments, an AAV ITR of the disclosure is about 70%, about 75%, about 80%, about 85%, about 90%, about 95%, or about 99% identical to an ITR having a nucleic acid sequence of any one of SEQ ID NOs: 1-4. In some embodiments, an ITR is about 70%, about 75%, about 80%, about 85%, about 90%, about 95%, or about 99% identical to an ITR having a nucleic acid sequence of SEQ ID NO: 1. In some embodiments, an ITR is about 70%, about 75%, about 80%, about 85%, about 90%, about 95%, or about 99% identical to an ITR having a nucleic acid sequence of SEQ ID NO: 2. In some embodiments, an ITR is about 70%, about 75%, about 80%, about 85%, about 90%, about 95%, or about 99% identical to an ITR having a nucleic acid sequence of SEQ ID NO: 3. In some embodiments, an ITR is about 70%, about 75%, about 80%, about 85%, about 90%, about 95%, or about 99% identical to an ITR having a nucleic acid sequence of SEQ ID NO: 4.

Except for a small number of unpaired bases (e.g., 7 unpaired bases), an ITR sequence is self-complementary and forms an energetically stable "T" shaped hairpin ($\Delta G \approx -72.4$ kcal per mol, Tm>80° C.). An AAV ITR can exist in two conformations: "flip" and "flop", which are a result of the rolling hairpin mechanism of AAV replication. During virus DNA replication, the cellular DNA polymerase complex initiates synthesis at the 3'-terminus of the template strand where the partial duplex formed by the ITR serves as the primer for primer extension. The replicative intermediate formed is an intramolecular duplex with the template and nascent strands covalently connected by the ITR. During a productive infection, a process called terminal resolution resolves the intra-strand ITR resulting in two full-length, complementary virus genomes.

In some embodiments, novel ITRs (e.g., AAV8 or AAVrh.39 ITRs, e.g., any one of SEQ ID NOs: 1-4) can be used to develop new "hybrid" ITR constructs to improve vector production, manufacturing, and in vivo performance. AAV ITRs interact with a number of host proteins and can trigger anti-viral and DNA damage response pathways. AAV vectors based on new hybrid ITR constructs have the potential to dampen host anti-viral and DNA damage-responses.

For example, a hybrid ITR construct may comprise an AAV8 ITR (e.g., a AAV8 5' ITR or an AAV8 3' ITR) and a non-AAV8 ITR. In some embodiments, a hybrid ITR construct comprises an AAV8 ITR and an AAVrh.39 ITR. In some embodiments, a hybrid ITR construct comprises an AAV8 5' ITR and an AAVrh.39 3' ITR. In some embodiments, a hybrid ITR construct comprises an AAV8 3' ITR and an AAVrh.39 5' ITR. In some embodiments, a hybrid ITR construct comprises an AAV8 ITR and an AAV2 ITR. In some embodiments, a hybrid ITR construct comprises an AAV8 5' ITR and a 3' AAV2 ITR. In some embodiments, a hybrid ITR construct comprises an AAV8 3' ITR and an AAV2 5' ITR.

In some embodiments, a hybrid ITR construct comprises an AAVrh.39 ITR (e.g., an AAVrh.39 5' ITR or an AAVrh.39 3' ITR) and a non-AAVrh.39 ITR. In some embodiments, a hybrid ITR construct comprises an AAVrh.39 ITR and an AAV2 ITR. In some embodiments, a hybrid ITR construct comprises an AAVrh.39 5' ITR and a 3' AAV2 ITR. In some embodiments, a hybrid ITR construct comprises an AAVrh.39 3' ITR and an AAV2 5' ITR.

In some embodiments, an AAV inverted terminal repeat sequence (e.g., an AAV8 ITR or and AAVrh.39 ITR) is an interrupted self-complementary sequence. Aspects of the disclosure include interrupted self-complementary nucleic acid sequences comprising an operative terminal resolution site (trs) that are useful for the formation of closed-ended linear duplex DNA (ceDNA). Typically, replication of nucleic acids comprising interrupted self-complementary nucleic acid sequences (e.g., AAV ITRs, e.g., comprising any one of SEQ ID NOs: 1-4) is initiated from the 3' end of the cross-arm (e.g., hairpin structure) and generates a duplex molecule in which one of the ends is covalently closed; the covalently closed ends of the duplex molecule are then cleaved by a process called terminal resolution to form a two separate single-stranded nucleic acid molecules. Without wishing to be bound by any particular theory, the process of terminal resolution is mediated by a site- and strand-specific endonuclease cleavage at a terminal resolution site (trs) (e.g., a rolling circle replication protein, such as AAV Rep protein). Examples of trs sequences include 3'-CCGGTTG-5' and 5'-AGTTGG-3'. It has been hypothesized that Rep-mediated strand nicking takes place between the central di-thymidine ("TT") portion of the trs sequence. Therefore, in some embodiments, the operative terminal resolution site comprises a sequence 5'-TT-3'.

Aspects of the disclosure relate to the positioning of a terminal resolution site (trs) relative to a rolling circle replication protein binding element. Generally, a trs is positioned upstream (e.g., 5') relative to a rolling circle replication protein binding element. However, in some embodiments, a trs is positioned downstream (e.g., 3') relative to a rolling circle replication protein binding element. In some embodiments, the 3' end of the operative terminal resolution site is 15 to 25 nucleotides (e.g., 15, 16, 17, 18, 19, 20, 21, 22, 23, 24, or 25 nucleotides) from the 5' end of the rolling circle replication protein binding element.

In the absence of AAV cap gene expression, an AAV vector genome having asymmetrical ITRs undergoes inefficient replication, and the replication products accumulate in a novel conformation of closed-ended linear duplex DNA (ceDNA). Due to inefficient replication (e.g., incomplete terminal resolution), the complementary strands of the intramolecular intermediate are now covalently linked through the ITRs on both ends of the genome. Thus, in native conditions, ceDNA behaves as linear duplex DNA, however, in denaturing conditions, ceDNA strands melt apart, but remain linked, therefore transforming the linear duplex molecule into single-stranded circular DNA.

In some embodiments, ceDNA production from asymmetric AAV ITRs is dependent on a truncated ITR at one end and an operative (e.g., functional) ITR (e.g., an ITRs comprising any one of SEQ ID NOs: 1-4) on the opposite end of the transgene cassette. In some embodiments, the truncated ITR is inefficiently processed during the replication cycles of ceDNA in host cells leading to an accumulation of replication intermediates, duplex monomer, duplex dimers, etc. In the absence of structural (capsid or cap) protein expression, a Rep protein (e.g., Rep 78 or Rep 68) assembles on the intact ITRs and catalyze the site-specific nicking at the terminal resolution site. The reaction results in the formation of a transient tyrosine-phosphodiester between a tyrosine of the Rep protein and a thymidine of the terminal resolution site of the ITS. The transient nucleoprotein complex then transfers the donor strand to the free 3'-terminus of the complementary strand. The ceDNA conformation therefore, results from the defective ITR on one end of the vector genome, an intact or operative ITR on the opposite end, and the co-expression of the Rep proteins (e.g., p5 and p19 Rep proteins, where at least one p5 and one p19 Rep are expressed). Other parvovirus "small" Rep or NS proteins can substitute for AAV p19 Rep protein (Rep 52 and Rep 40). Since these small Rep proteins are non-processive, monomeric helicases, it is feasible that non-parvoviridae super family 2 (SF2) helicases can substitute for the AAV Rep proteins.

In some embodiments, a Rep protein is a Rep78, Rep68, Rep52, or Rep 40 protein. In some embodiments, an AAV8 Rep78 protein comprises the amino acid sequence as set forth in SEQ ID NO: 7. In some embodiments, an AAV8 Rep68 protein comprises the amino acid sequence as set forth in SEQ ID NO: 8. In some embodiments, an AAV8 Rep52 protein comprises the amino acid sequence as set forth in SEQ ID NO: 9. In some embodiments, an AAV8 Rep40 protein comprises the amino acid sequence as set forth in SEQ ID NO: 10. In some embodiments, an AAVrh.39 Rep78 protein comprises the amino acid sequence as set forth in SEQ ID NO: 11. In some embodiments, an AAVrh.39 Rep68 protein comprises the amino acid sequence the set forth in SEQ ID NO: 12. In some embodiments, an AAVrh.39 Rep52 protein comprises the amino acid sequence as set forth in SEQ ID NO: 13. In some embodiments, an AAVrh.39 Rep40 protein comprises the amino acid sequence as set forth in SEQ ID NO: 14.

In some embodiments, a cap protein is an AAV8 cap protein. In some embodiments, an AAV8 cap protein comprises the amino acid sequence as set forth in SEQ ID NO: 15. In some embodiments, a cap protein is an AAVrh.39 cap protein. In some embodiments, an AAVrh.39 cap protein comprises the amino acid sequence as set forth in SEQ ID NO: 16.

Recombinant AAV (rAAV) vectors of the disclosure are typically composed of, at a minimum, a transgene and its regulatory sequences, and 5' and 3' AAV ITRs (e.g., AAV ITRs comprising any one of SEQ ID NOs: 1-4). In some embodiments, a recombinant AAV vector is packaged into a capsid protein and delivered to a selected target cell. In some embodiments, the transgene is a nucleic acid sequence, heterologous to the vector sequences, that encodes a polypeptide, protein, functional RNA molecule (e.g., miRNA, miRNA inhibitor) or other gene product, of interest. The nucleic acid coding sequence is operatively linked to regulatory components in a manner that permits transgene transcription, translation, and/or expression in a cell of a target tissue.

The AAV sequences of the vector comprise the cis-acting 5' and 3' inverted terminal repeat sequences (e.g., comprising any one of SEQ ID NOs: 1-4). In some embodiments, the ITR sequences are about 145 bp in length. Preferably, substantially the entire sequences encoding the ITRs are used in the molecule, although some degree of minor modification of these sequences is permissible. The ability to modify nucleic acid sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences.

As used herein, the term "flanked" refers to the positioning of a first interrupted self-complementary sequence upstream (e.g., 5') relative to a heterologous nucleic acid insert and a second interrupted self-complementary sequence downstream (e.g., 3') relative to the heterologous nucleic acid insert. For example, an adeno-associated virus genome comprises open reading frames of the rep and cap genes "flanked" by inverted terminal repeats (ITRs).

As used herein, the term "operative" refers to the ability of a nucleic acid sequence to perform its intended function. For example, an "operative binding region" is a nucleic acid sequence that retains binding function for its intended target (e.g., a protein or nucleic acid). In another example, an "operative cleavage site" is a nucleic acid sequence that retains its ability to be specifically cleaved by a particular enzyme or enzymes.

In some embodiments, the disclosure provides a self-complementary AAV vector. As used herein, the term "self-complementary AAV vector" (scAAV) refers to a vector containing a double-stranded vector genome generated by the absence of a terminal resolution site (TR) from one of the ITRs (e.g., an ITR comprising any one of SEQ ID NOs: 1-4). The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle.

In some embodiments, the rAAVs of the present disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeat (ITR) of one AAV serotype and a capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In some embodiments, the rAAVs of the present disclosure comprise at least one AAV8 ITR sequence and an AAV8 capsid protein. In some embodiments, an rAAV comprises two AAV8 ITR sequences (an AAV8 5' ITR and an AAV8 3' ITR) and an AAV8 capsid protein. In some embodiments, an rAAV comprises an AAV8 ITR sequence, an AAVrh.39 ITR sequence, and an AAV8 capsid protein. In some embodiments, an rAAV comprises an AAV8 5' ITR sequence, an AAVrh.39 3' ITR sequence, and an AAV8 capsid protein. In some embodiments, an rAAV comprises an AAV8 3' ITR sequence, an AAVrh.39 5' ITR sequence, and an AAV8 capsid protein.

In some embodiments, the rAAVs of the present disclosure comprise at least one AAVrh.39 ITR sequence and an AAVrh.39 capsid protein. In some embodiments, an rAAV comprises two AAVrh.39 ITR sequences (an AAVrh.39 5' ITR and an AAVrh.39 3' ITR) and an AAVrh.39 capsid protein. In some embodiments, an rAAV comprises an AAV8 ITR sequence, an AAVrh.39 ITR sequence, and an AAVrh.39 capsid protein. In some embodiments, an rAAV comprises an AAV8 5' ITR sequence, an AAVrh.39 3' ITR sequence, and an AAVrh.39 capsid protein. In some embodiments, an rAAV comprises an AAV8 3' ITR sequence, an AAVrh.39 5' ITR sequence, and an AAVrh.39 capsid protein.

As used here, "rolling circle replication protein binding element" refers to a conserved nucleic acid sequence (e.g., motif) that is recognized and bound by a rolling circle replication protein, which is a viral nonstructural protein (NS protein) that initiates rolling circle (e.g., rolling hairpin) replication. Rolling circle (e.g., rolling hairpin) replication is described by Tattersall et al. Nature 2009, 263, pp. 106-109. Examples of NS proteins include, but are not limited to AAV Rep proteins (e.g., Rep78, Rep68, Rep52, Rep40), parvovirus nonstructural proteins (e.g., NS2), rotavirus nonstructural proteins (e.g., NSP1), and densovirus nonstructural proteins (e.g., PfDNV NS1). In some embodiments, the rolling circle replication protein binding element is a Rep binding element (RBE). In some embodiments, the RBE comprises the sequence 5'-GCTCGCTCGCTC-3' (SEQ ID NO: 18).

In some embodiments, rolling circle replication proteins are from the dependoparvovirus genus of the Parvoviridae family of viruses with linear single-stranded DNA genomes. In some embodiments, the rolling circle replication proteins are from the genera of the autonomous Parvovirinae including mice minute virus, Aleutian mink disease virus, bovine parvovirus, canine parvovirus, chicken parvovirus, feline panleukopenia virus, feline parvovirus, goose parvovirus, HB parvovirus, H-1 parvovirus, Kilham rat virus, lapine parvovivirus, LUIII virus, mink enteritis virus, mouse parvovirus, porcine parvovirus, raccoon parvovivurs, RT parvovirus, Tumor virus X, rat parvovirus 1a, barbarie duck parvovirus, equine parvovirus, hamster parvovirus, and rheumatorid arthritis virus 1. In some embodiments, the genus is parvovirus. In some embodiments, the rolling circle replication proteins are from the genera of Densovirinae including brevidensovirus, densovirus, and iteravirus.

In some embodiments, a rolling circle replication protein is from the genera of the subfamily Parvovirinae. Examples of Parvovirinae genera include but are not limited to Amdoparvovirus, Aveparvovirus, Bocaparvovirus, Copiparvovirus, Dependoparvovirus, Erythroparvovirus, Protoparvovirus, and Tetraparvovirus. In some embodiments, the rolling circle replication proteins are from the genera of the subfamily, Densovirinae. Examples of Densovirinae genera include but are not limited to Amdoparvovirus, Aveparvovirus, Bocaparvovirus, Copiparvovirus, Dependoparvovirus, Erythroparvovirus, Protoparvovirus, and Tetraparvovirus. In some embodiments, the rolling circle replication protein(s) is from a Dependovirus, such as Adeno-associated virus 2 (AAV2), Adeno-associated virus 3 (AAV3), Adeno-associated virus 4 (AAV4), or Adeno-associated virus 5 (AAV5), or any combination thereof.

In some embodiments, the rolling circle replication proteins are derived from the single-stranded DNA bacteriophage families. In some embodiments, the virus families are the Microviridae and the Inoviridae. In some embodiments, the rolling circle replication proteins are derived from Gram positive bacteria.

In addition to the major elements identified above for the nucleic acid, the nucleic acid also includes conventional control elements necessary which are operably linked to the heterologous nucleic acid insert (e.g., transgene) in a manner which permits its transcription, translation and/or expression in a cell transfected with a nucleic acid described by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

In some embodiments, a heterologous nucleic acid insert (e.g., transgene) comprises a protein coding sequence that is operably linked to one or more regulatory sequences. As used herein, a nucleic acid coding sequence and regulatory sequences are said to be "operably" linked when they are covalently linked in such a way as to place the expression or transcription of the nucleic acid sequence (e.g., transgene) under the influence or control of the regulatory sequences. If it is desired that the nucleic acid sequence (e.g., transgene) be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

In some embodiments, proteins and nucleic acids of the disclosure are isolated. As used herein, the term "isolated" means artificially produced. In some embodiments, with respect to nucleic acids, the term "isolated" refers to a nucleic acid that is: (i) amplified in vitro by, for example, polymerase chain reaction (PCR); (ii) recombinantly produced by molecular cloning; (iii) purified, as by restriction endonuclease cleavage and gel electrophoretic fractionation, or column chromatography; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

For nucleic acids (e.g., transgenes) encoding proteins, a polyadenylation sequence generally is inserted following the transgene sequences and before the 3' AAV ITR sequence. A heterologous nucleic acid insert (e.g., transgene) useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al, Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

The composition of the transgene sequence (e.g., heterologous nucleic acid insert) of the nucleic acid will depend upon the use to which the resulting nucleic acid will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

In some embodiments, a transgene (e.g., heterologous nucleic acid insert) flanked by ITRs ranges from about 10 to about 5,000 base pairs, about 10 to about 10,000 base pairs, about 10 to about 50,000 base pairs in length. In some embodiments, a transgene (e.g., heterologous nucleic acid insert) flanked by ITRs ranges from about 10 to about 50 base pairs in length. In some embodiments, a transgene (e.g., heterologous nucleic acid insert) flanked by ITRs ranges from about 20 to about 100 base pairs in length. In some embodiments, a transgene (e.g., heterologous nucleic acid insert) flanked by ITRs ranges from about 500 to about 1500 base pairs in length. In some embodiments, a transgene (e.g., heterologous nucleic acid insert) flanked by ITRs ranges from about 1000 to about 5000 base pairs in length. In some embodiments, the size of a transgene (e.g., heterologous nucleic acid insert) exceeds the capacity of a traditional AAV vector (e.g., exceeds about 4.8 kb).

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of a nucleic acid.

In some aspects, the disclosure provides nucleic acids for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of nucleic acid (e.g., a nucleic acid as described by the disclosure) that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of nucleic acids (e.g., nucleic acids as described by the disclosure) encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The nucleic acids (e.g., nucleic acids as described by the disclosure) may comprise a gene to be transferred (e.g., expressed in) to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; omithine transcarbamylase, associated with omithine transcarbamylase deficiency; argininosuccinic acid synthetase, associated with citrullinemia; low density lipoprotein receptor protein, associated with familial hypercholesterolemia;

UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

The nucleic acids of the disclosure (e.g., nucleic acid having a heterologous nucleic acid insert) can be used to restore the expression of genes that are reduced in expression, silenced, or otherwise dysfunctional in a subject (e.g., a tumor suppressor that has been silenced in a subject having cancer). The nucleic acids of the disclosure can also be used to knockdown the expression of genes that are aberrantly expressed in a subject (e.g., an oncogene that is expressed in a subject having cancer). In some embodiments, a heterologous nucleic acid insert encoding a gene product associated with cancer (e.g., tumor suppressors) may be used to treat the cancer, by administering nucleic acid comprising the heterologous nucleic acid insert to a subject having the cancer. In some embodiments, a nucleic acid comprising a heterologous nucleic acid insert encoding a small interfering nucleic acid (e.g., shRNAs, miRNAs) that inhibits the expression of a gene product associated with cancer (e.g., oncogenes) may be used to treat the cancer, by administering nucleic acid comprising the heterologous nucleic acid insert to a subject having the cancer. In some embodiments, nucleic comprising a heterologous nucleic acid insert encoding a gene product associated with cancer (or a functional RNA that inhibits the expression of a gene associated with cancer) may be used for research purposes, e.g., to study the cancer or to identify therapeutics that treat the cancer.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-

3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-29-p, hsa-miR-22, hsa-miR-22*, hsa-miR-220a, hsa-miR-220b, hsa-miR-220c, sa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26-2*, hsa-miR-26b, hsa-miR-26b*, hsa-miR-27a, hsa-miR-27a*, hsa-miR-2 97, hsa-miR-2*, hsa-miR-28-93p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsamiR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a nucleic acid, as discussed above. MicroRNA sponges specifically inhibit miRNAs through a complementary heptameric seed sequence (Ebert, M. S. Nature Methods, Epub Aug. 12, 2007). In some embodiments, an entire family of miRNAs can be silenced using a single sponge sequence. TuD RNAs achieve efficient and long-term-suppression of specific miRNAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art.

In some embodiments, nucleic acids described herein (e.g., a nucleic acid having an ITR comprising any one of SEQ ID NOs: 1-4) may be useful for delivering gene editing molecules (e.g., nucleases) to a subject. In some embodiments a nucleic acid described by the disclosure comprises a heterologous nucleic acid insert encodes a nuclease. As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), engineered meganucleases and CRISPR-associated proteins (Cas nucleases). In some embodiments, the nuclease is a ZFN. In some embodiments, the ZFN comprises a FokI cleavage domain. In some embodiments, the ZFN comprises Cys2His2 fold group. In some embodiments, the nuclease is a TALEN. In some embodiments, the TALEN comprises a FokI cleavage domain. In some embodiments, the nuclease is an engineered meganuclease.

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, Cas6 and dCas9. dCas9 is an engineered Cas protein that binds to a target locus but does not cleave said locus. In some embodiments, the nuclease is Cas9. In some embodiments, the Cas9 is derived from the bacteria *S. pyogenes* (SpCas9).

For the purpose of genome editing, the CRISPR system can be modified to combine the tracrRNA and crRNA in to a single guide RNA (sgRNA) or just (gRNA). As used herein, the term "guide RNA" or "gRNA" refers to a polynucleotide sequence that is complementary to a target sequence in a cell and associates with a Cas nuclease, thereby directing the Cas nuclease to the target sequence. In some embodiments, a nucleic acid described by the disclosure comprises a heterologous nucleic acid insert encoding a guide RNA (gRNA). In some embodiments, a gRNA ranges between 1 and 30 nucleotides in length. In some embodiments, a gRNA ranges between 5 and 25 nucleotides in length. In some embodiments, a gRNA ranges between 10 and 20 nucleotides in length. In some embodiments, a gRNA ranges between 14 and 18 nucleotides in length. In some embodiments, a nucleic acid described by the disclosure comprises a heterologous nucleic acid insert encoding a gRNA and a CRISPR nuclease.

In some aspects, the disclosure relates to a nucleic acid encoding a heterologous nucleic acid insert that does not encode a functional protein. For example, in the context of gene therapy, transgene promoter integration may cause oncogene activation. Accordingly, in some embodiments, the disclosure relates to a heterologous nucleic acid insert encoding a promoterless construct. Without wishing to be bound by any particular theory, a promoterless expression construct is useful, in some embodiments, as a substrate for gene editing.

As used herein, "genome editing" refers to adding, disrupting or changing genomic sequences (e.g., a gene sequence). In embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases, the CRISPR/Cas system. In some embodiments, the gene editing technologies are proteins or molecules related to TALENs, including but not limited to transcription activator-like effectors (TALEs) and restriction endonucleases (e.g., FokI). In some embodiments, the gene editing technologies are proteins or molecules related to ZFNs, including but not limited to proteins comprising the Cys2His2 fold group (for example Zif268 (EGR1)), and restriction endonucleases (e.g., FokI). In some embodiments, the gene editing technologies are proteins or molecules related to the CRISPR/Cas system, including but not limited to Cas9, Cas6, dCas9, CRISPR RNA (crRNA) and trans-activating crRNA (tracrRNA). In some embodiments, the promoterless construct provides a substrate for TALENS, zinc finger nucleases (ZFNs), meganucleases, Cas9, and other gene editing proteins.

In some aspects, the disclosure relates to a nucleic acid encoding a heterologous nucleic acid insert that encodes a DNA or mRNA vaccine. As used herein, "DNA vaccine" or "mRNA vaccine" refers to a nucleic acid encoding an antigen that stimulates an immune response (e.g., a cellular immune response or a humoral immune response) against that antigen in a host. In some embodiments, the immune response is a protective response that protects against a future infection or condition. However, in some embodiments, the immune response treats (e.g., eradicates or attenuates) an existing infection or condition. Examples of DNA vaccines include HL chain Ig, scFv, single-domain Ig derived from camelidae (VhH) or cartilaginous fish (Vnar), nanobody, and other paratope recognitions peptides and fusion peptides collectively referred to as Ig (or Ig-like) molecules.

In some embodiments, a heterologous nucleic acid insert encodes an Ig or Ig-like molecule. In some embodiments, the Ig (or Ig-like) molecules are unmodified protein sequences derived from monoclonal antibody sequences. In some embodiments, the Ig (or Ig-like) molecules are unmodified protein sequences derived from murine or other mammalian monoclonal antibody sequences.

In some embodiments, the Ig (or Ig-like) molecules are unmodified protein sequences derived from synthetic randomly generated peptide libraries. In some embodiments, the libraries were derived from complimentary DNA obtained from naïve vertebrate species. The species include, but are not limited to mammals, such as primates (e.g., humans and non-human primates), rodents (e.g., mouse, rats), ungulates, camelids, equines, canines, felines, marsupials, and animals of agricultural interest; Avian species, including chickens, ducks, and geese; piscine species including cartilaginous fish, lamprey eels, and jawed fish species.

In some embodiments, the heterologous nucleic acid encodes the heavy and light chains for an immunoglobulin (Ig), such that when administered to a permissive cell, an assembled Ig is secreted into the circulatory system. In some embodiments, the Ig molecule is not secreted and acts internally as a so-called "intra-body". In some embodiments, a heterologous nucleic acid insert encodes an Ig molecule that is an engineered single-chain antibody consisting of the heavy and light chain variable regions in one polypeptide (scFv). The scFv retains avidity and specificity for the target antigen.

In some embodiments, a heterologous nucleic acid insert encodes an Ig molecule that binds to microbial agents and affects the infectivity of the microbe. In some embodiments, the microbial agents are prokaryotic organisms. In some embodiments, the microbial agents are *Rickettsia, Mycoplasma*, or other intracellular life forms.

In some embodiments, a heterologous nucleic acid insert encodes an Ig molecule that binds to viral structural protein(s) of human pathogenic viruses, including but not limited an Ebola virus viral protein, a human immune deficiency viral protein, a papilloma viral protein, a herpes simplex 1 viral protein, a herpes simplex 2 viral protein, a HCV A viral protein, a HCV B viral protein, a HCV C viral protein, a HCV non-A viral protein, a HCV non-B viral protein, or a dengue hemorrhagic fever viral protein. In some embodiments, a heterologous nucleic acid insert encodes an Ig molecule that binds to viral structural protein(s) of a zoonotic pathogen, including, but not limited to foot and mouth disease virus and rabies virus.

In some aspects, the disclosure relates to isolated nucleic acids comprising a transgene encoding one or more miRNA binding sites. Without wishing to be bound by any particular theory, incorporation of miRNA binding sites into gene expression constructs allows for regulation of transgene expression (e.g., inhibition of transgene expression) in cells and tissues where the corresponding miRNA is expressed. In some embodiments, incorporation of one or more miRNA binding sites into a transgene allows for de-targeting of transgene expression in a cell-type specific manner. In some embodiments, one or more miRNA binding sites are positioned in a 3' untranslated region (3' UTR) of a transgene, for example between the last codon of a nucleic acid sequence encoding a therapeutic protein or variant thereof, and a poly A sequence.

In some embodiments, a transgene comprises one or more (e.g., 1, 2, 3, 4, 5, or more) miRNA binding sites that de-target expression of the therapeutic protein from liver cells. For example, in some embodiments, a transgene comprises one or more miR-122 binding sites. In some embodiments, a transgene comprises one or more miR-142 binding sites.

In some embodiments, a transgene comprises one or more (e.g., 1, 2, 3, 4, 5, or more) miRNA binding sites that de-target expression of therapeutic proteins from immune cells (e.g., antigen presenting cells (APCs), such as macrophages, dendrites, etc.). Incorporation of miRNA binding sites for immune-associated miRNAs may de-target transgene (e.g., one or more therapeutic proteins) expression from antigen presenting cells and thus reduce or eliminate immune responses (cellular and/or humoral) produced in the subject against products of the transgene, for example as described in US 2018/0066279, the entire contents of which are incorporated herein by reference.

As used herein an "immune-associated miRNA" is a miRNA preferentially expressed in a cell of the immune system, such as an antigen presenting cell (APC). In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152. In some embodiments, a transgene described herein comprises one or more binding sites for miR-142.

In some aspects, nucleic acids described by the disclosure are useful for the production of modified cells, such as ex vivo modified cells. As used herein, "ex vivo modified cell" refers to a cell (e.g., a mammalian cell) that is removed from a subject, genetically modified (e.g., transfected or transduced with exogenous nucleic acids, or genetically reprogrammed), cultured or expanded, and optionally, returned to a subject (e.g., either the same subject, or a different subject). Generally, ex vivo modified cells are useful for autologous cell therapy, or allogeneic cell therapy. For example, cells may be removed from a subject having a disease associated with a particular genetic defect (e.g., overexpression of a particular protein), transfected with a nucleic acid that corrects the genetic defect (e.g. reduces expression of the protein), and reintroduced into the subject. In another non-limiting example, cells are removed from a subject, genetically reprogrammed (e.g., dedifferentiated or transdifferentiated into stem cells), expanded, and reintroduced into the subject. In some embodiments, ex vivo modified cells produced by transfection with a nucleic acid as described by the disclosure have an improved safety profile compared to ex vivo cells produced by currently available gene therapy vectors.

In some aspects, nucleic acids described by the disclosure are useful for the production of chimeric antigen T-cells (CARTs). Chimeric Antigen Receptors (CARs) are engineered T cell receptors displaying specificity against target antigens based on a single chain FV (scFv) antibody moiety. Generally, CARTs are produced by transduction of T-cells with lentiviral vectors comprising DNA encoding CARs. Lentiviral transduction, in some embodiments, raises the risk of insertional mutagenesis leading to cancer. As described by the disclosure, nucleic acids having asymmetric interrupted self-complementary sequences exhibit reduced likelihood of insertional mutagenesis compared to other gene therapy modalities. Accordingly, in some embodiments a nucleic acid described by the disclosure comprises a heterologous nucleic acid insert (e.g., a transgene) encoding a CAR. In some embodiments, a CART produced by transduction with a nucleic acid described by the disclosure exhibits an improved safety profile compared to a CART produced by lentiviral transduction.

The nucleic acid, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the nucleic acids (e.g., a nucleic acid having an ITR comprising any one of SEQ ID NOs: 1-4) to a mammalian subject may be by, for example, intramuscular injection or by administration into the bloodstream of the mammalian subject. Administration into the bloodstream may be by injection into a vein, an artery, or any other vascular conduit. In some embodiments, the nucleic acids are administered into the bloodstream by way of isolated limb perfusion, a technique well known in the surgical arts, the method essentially enabling the artisan to isolate a limb from the systemic circulation prior to administration of the nucleic acid. A variant of the isolated limb perfusion technique, described in U.S. Pat. No. 6,177,403, can also be employed by the skilled artisan to administer the nucleic acid(s) into the vasculature of an isolated limb to potentially enhance transfection of muscle cells or tissue. Moreover, in certain instances, it may be desirable to deliver the nucleic acid(s) to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat.

Genet. 3:219-223, 1993; and Alisky and Davidson, Hum. Gene Ther. 11:2315-2329, 2000).

Suitable carriers may be readily selected by one of skill in the art in view of the indication for which the nucleic acid(s) is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the nucleic acid(s) and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The nucleic acid(s) are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of nucleic acid(s) required to achieve a particular "therapeutic effect," will vary based on several factors including, but not limited to: the route of nucleic acid administration, the level of gene or RNA expression required to achieve a therapeutic effect, the specific disease or disorder being treated, and the stability of the gene or RNA product. One of skill in the art can readily determine a nucleic acid dose range to treat a patient having a particular disease or disorder based on the aforementioned factors, as well as other factors that are well known in the art.

Dosage regime may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the nucleic acid-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver nucleic acids. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuumdrying and freeze-drying techniques which yield a powder of the active ingredient plus any additional desired ingredient from a previously sterile-filtered solution thereof.

The nucleic acid compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the nucleic acids may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 ANG., containing an aqueous solution in the core.

In some embodiments, a liposome comprises cationic lipids. The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In some embodiments, cationic lipids include saturated and unsaturated alkyl and alicyclic ethers and esters of amines, amides, or derivatives thereof. In some embodiments, cationic lipids comprise straight-chain, branched alkyl, alkenyl groups, or any combination of the foregoing. In some embodiments, cationic lipids contain from 1 to about 25 carbon atoms (e.g., 1, 2, 3, 4, 5, 6, 7, 8, 9, 10, 11, 12, 13, 14, 15, 16, 17, 18, 19, 20, 21, 22, 23, 24, or 25 carbon atoms. In some embodiments, cationic lipids contain more than 25 carbon atoms. In some embodiments, straight chain or branched alkyl or alkene groups have six or more carbon atoms. A cationic lipid may also comprise, in some embodiments, one or more alicyclic groups. Non-limiting examples of alicyclic groups include cholesterol and other steroid groups. In some embodiments, cationic lipids are prepared with a one or more counterions. Examples of counterions (anions) include but are not limited to Cl—, Br—, I—, F—, acetate, trifluoroacetate, sulfate, nitrite, and nitrate.

Non-limiting examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N, N,N-trimethylammonium methylsulfate (DOTAP), 3β-[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Nucleic acids (e.g., a nucleic acid having an ITR comprising any one of SEQ ID NOs: 1-4) can also be complexed with, e.g., poly (L-lysine) or avidin and lipids may, or may not, be included in this mixture, e.g., stearyl-poly (L-lysine).

In some embodiments, a nucleic acid described by the disclosure is delivered using a cationic lipid described in U.S. Pat. No. 8,158,601, or a polyamine compound or lipid as described in U.S. Pat. No. 8,034,376, the contents of each of which are incorporated herein by reference.

In some embodiments, a nucleic acid described by the disclosure is conjugated (e.g., covalently bound to an agent that increases cellular uptake. An "agent that increases cellular uptake" is a molecule that facilitates transport of a nucleic acid across a lipid membrane. For example, a nucleic acid may be conjugated to a lipophilic compound (e.g., cholesterol, tocopherol, etc.), a cell penetrating peptide (CPP) (e.g., penetratin, TAT, Syn1B, etc.), and polyamines (e.g., spermine). Further examples of agents that increase cellular uptake are disclosed, for example, in Winkler (2013). Oligonucleotide conjugates for therapeutic applications. Ther. Deliv. 4(7); 791-809, the contents of which are incorporated herein by reference.

In some embodiments, a nucleic acid described by the disclosure is conjugated to a polymer (e.g., a polymeric molecule) or a folate molecule (e.g., folic acid molecule). Generally, delivery of nucleic acids conjugated to polymers is known in the art, for example as described in WO2000/34343 and WO2008/022309, the contents of which are incorporated herein by reference. In some embodiments, a nucleic acid described by the disclosure is conjugated to a poly(amide) polymer, for example as described by U.S. Pat. No. 8,987,377. In some embodiments, a nucleic acid described by the disclosure is conjugated to a folic acid molecule as described in U.S. Pat. No. 8,507,455, the contents of which are incorporated herein by reference.

In some embodiments, a nucleic acid described by the disclosure is conjugated to a carbohydrate, for example as described in U.S. Pat. No. 8,450,467, the contents of which are incorporated herein by reference.

Alternatively, nanocapsule formulations of the nucleic acid may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In some embodiments, a nucleic acid described by the disclosure is delivered by a lipid nanoparticle. Generally, lipid nanoparticles comprise an ionizable amino lipid (e.g., heptatriaconta-6,9,28,31-tetraen-19-yl 4-(dimethylamino)butanoate, DLin-MC3-DMA, a phosphatidylcholine (1,2-distearoyl-sn-glycero-3-phosphocholine, DSPC), cholesterol and a coat lipid (polyethylene glycol-dimyristoyl-glycerol, PEG-DMG), for example as disclosed by Tam et al. (2013). Advances in Lipid Nanoparticles for siRNA delivery. Pharmaceuticals 5(3): 498-507. In some embodiments, a lipid nanoparticle has a mean diameter between about 10 and about 1000 nm. In some embodiments, a lipid nanoparticle has a diameter that is less than 300 nm. In some embodiments, a lipid nanoparticle has a diameter between about 10 and about 300 nm. In some embodiments, a lipid nanoparticle has a diameter that is less than 200 nm. In some embodiments, a lipid nanoparticle has a diameter between about 25 and about 200 nm. In some embodiments, a lipid nanoparticle preparation (e.g., composition comprising a plurality of lipid nanoparticles) has a size distribution in which the mean size (e.g., diameter) is about 70 nm to about 200 nm, and more typically the mean size is about 100 nm or less.

In some embodiments, a nucleic acid described by the disclosure is delivered by a gold nanoparticle. Generally, a nucleic acid can be covalently bound to a gold nanoparticle or non-covalently bound to a gold nanoparticle (e.g., bound by a charge-charge interaction), for example as described by Ding et al. (2014). Gold Nanoparticles for Nucleic Acid Delivery. Mol. Ther. 22(6); 1075-1083. In some embodiments, gold nanoparticle-nucleic acid conjugates are produced using methods described, for example, in U.S. Pat. No. 6,812,334, the contents of which are incorporated herein by reference.

In addition to the methods of delivery described above, the following techniques are also contemplated as alternative methods of delivering the nucleic acid compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

In some embodiments, the disclosure provides a method of delivering a heterologous nucleic acid to a cell (e.g., a host cell), the method comprising delivering to the cell a nucleic acid as described by the disclosure.

In some aspects, the disclosure provides transfected host cells. A "host cell" refers to any cell that harbors, or is capable of harboring, a substance of interest. A host cell may be used as a recipient of a nucleic acid as described by the disclosure. The term includes the progeny of the original cell which has been transfected. Thus, a "host cell" as used herein may refer to a cell which has been transfected with an exogenous DNA sequence (e.g., a nucleic acid as described by the disclosure). It is understood that the progeny of a single parental cell may not necessarily be completely identical in morphology or in genomic or total DNA complement as the original parent, due to natural, accidental, or deliberate mutation.

In some embodiments, a host cell is a bacterial cell. In some embodiments, a host cell is a HEK293 cell or is derived from a HEK293 cell. In some embodiments, a host cell is a permissive cell. In some embodiments, a host cell is not a permissive cell. Often a host cell is a mammalian cell. In some aspects, the disclosure provides a method of delivering a heterologous nucleic acid to a subject comprising administering a host cell having a nucleic acid as described by the disclosure to the subject. For example, in some embodiments, a host cell is a blood cell, such as a human blood cell, comprising a nucleic acid as described by the disclosure (e.g., a nucleic acid having a heterologous nucleic acid insert encoding a blood disease-associated transgene). Without wishing to be bound by any particular theory, delivery of such a host cell is useful, in some embodiments, for treatment of a disease or disorder.

Aspects of the disclosure relate to the discovery that nucleic acids as described herein elicit a reduced immune response (e.g., do not elicit an immune response) in a host relative to currently used viral and bacterially-derived gene therapy vectors. In some aspects, the disclosure provides a method of delivering a heterologous nucleic acid to a subject, the method comprising delivering to the subject a nucleic acid as described by the disclosure, wherein the delivery of the nucleic acid does not result in an immune response against the nucleic acid in the subject. In some embodiments, the immune response is a humoral response. Humoral immune response refers to production of antigen-specific antibodies by B lymphocytes. In some embodiments, the immune response is a cellular response. A cellular immune response refers to an immune response that does not involve antibodies but rather activation of immune cells (e.g., phagocytes, antigen-specific T-cells, macrophages, natural killer cells, etc.) by an antigen (e.g., an exogenous nucleic acid).

Without wishing to be bound by any particular theory, the lack of immune response elicited by administration of nucleic acids as described by the disclosure allows the nucleic acids to be administered to a host on multiple occasions. In some embodiments, the number of occasions in which a heterologous nucleic acid is delivered to a subject is in a range of 2 to 10 times (e.g., 2, 3, 4, 5, 6, 7, 8, 9, or 10 times). In some embodiments, a heterologous nucleic acid is delivered to a subject more than 10 times.

In some embodiments, a dose of nucleic acid (e.g., a nucleic acid having an ITR comprising any one of SEQ ID NOs: 1-4) is administered to a subject no more than once per calendar day (e.g., a 24-hour period). In some embodiments, a dose of nucleic acid is administered to a subject no more than once per 2, 3, 4, 5, 6, or 7 calendar days. In some embodiments, a dose of nucleic acid is administered to a subject no more than once per calendar week (e.g., 7 calendar days). In some embodiments, a dose of nucleic acid is administered to a subject no more than bi-weekly (e.g., once in a two calendar week period). In some embodiments, a dose of nucleic acid is administered to a subject no more than once per calendar month (e.g., once in 30 calendar days). In some embodiments, a dose of nucleic acid is administered to a subject no more than once per six calendar months. In some embodiments, a dose of nucleic acid is administered to a subject no more than once per calendar year (e.g., 365 days or 366 days in a leap year).

As disclosed herein nucleic acids (including DNA expression constructs that may be used to express them) may be administered by any suitable route. For use in therapy, an effective amount of the nucleic acid (e.g., oligonucleotide) and/or other therapeutic agent can be administered to a subject by any mode that delivers the agent to the desired tissue, e.g., muscle tissue. In some embodiments, agents (e.g., nucleic acids) are administered intramuscularly. Other suitable routes of administration include but are not limited to oral, parenteral, intravenous, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the agents can be formulated readily by combining the active compound(s) with pharmaceutically acceptable carriers well known in the art. Such carriers enable the agents of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally oral formulations may also be formulated in saline or buffers for neutralizing internal acid conditions or may be administered without any carriers.

Pharmaceutical preparations that can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. Formulations for oral administration are typically in dosages suitable for such administration.

For buccal administration, the compositions may take the form of tablets or lozenges formulated in conventional manner.

For administration by inhalation, agents (e.g., nucleic acids) for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The agents (e.g., nucleic acids), when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of agents (e.g., antisense nucleic acids) in water-soluble form. Additionally, suspensions of agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, agents (e.g., nucleic acids) may be in powder form for constitution with a suitable vehicle, e.g., sterile pyrogen-free water, before use. Agents (e.g., nucleic acids) may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the agents (e.g., antisense nucleic acids), increasing convenience to the subject and the physician. Many types of release delivery systems are available. They include polymer base systems such as poly(lactide glycolide), copolyoxalates, polycaprolactones, polyesteramides, polyorthoesters, polyhydroxybutyric acid, and polyanhydrides. Delivery systems also include non-polymer systems that are: lipids including sterols such as cholesterol, cholesterol esters and fatty acids or neutral fats such as mono, di, and tri glycerides; hydrogel release systems; silastic systems; peptide-based systems; wax coatings; compressed tablets using conventional binders and excipients; partially fused implants; and others disclosed herein.

EXAMPLES

Example 1

This example describes newly discovered ITR8 and ITRrh.39 sequences that are structurally and functionally distinct from previously described ITRs. In some embodiments, novel ITRs disclosed herein (or rAAVs comprising novel ITRs or combinations of novel ITRs and previously described ITRs, such as AAV2 ITR) can be used to develop new "hybrid" ITR vector constructs to improve vector production, manufacturing, and in vivo performance. Additionally, these new ITR sequences can be used in combination with different AAV rep and cap genes to develop the best combinations for efficient rAAV vector production.

AAV ITRs interact with a number of host proteins and can trigger anti-viral and DNA damage response pathways. AAV vectors based on new hybrid ITR constructs have the potential to dampen host anti-viral and DNA damage-responses.

Without wishing to be bound by any particular theory, rAAVs using hybrid/asymmetric ITR designs may have reduced ability to form intramolecular circular intermediates, with increased efficiency for directional tail-to-head intermolecular recombination of linear genomes capable of expressing dual-vector-encoded trans-spliced gene products, enhancing dual-vector gene delivery, and solving the 4.7-kb packaging limitation inherent to AAV vectors. In some embodiments, the ITRs may generate rAAV genomes with different in vivo episomal stabilities, integration profiles, and alternative genetic fates for different applications. The ITRs may also harbor promoter-like function with cell type-specific activities, and may confer unique/improved transgene expression profiles.

Example 2

Nucleic acid constructs comprising unique hybrid ITR sequences (combinations of 5' and 3' ITR sequences) were designed and tested for transgene expression. The transgene was either enhanced green fluorescent protein (eGFP) or human Alpha-1-antitrypsin (hA1AT). All designed constructs comprised one or more of, in 5'-to-3' direction, a variable 5' ITR sequence, a CMV immediate early enhancer, a chicken beta actin (CBA) promoter, a transgene, a rabbit globin poly A sequence, and a variable 3' ITR sequence.

TABLE 1

Nucleic acid constructs of Example 2 for expression of eGFP

| Description | 5' ITR sequence | 3' ITR sequence |
| --- | --- | --- |
| pAAV-2/2-(eGFP) | AAV2 5' ITR | AAV2 3' ITR |
| pAAV-2/8-(eGFP) | AAV2 5' ITR | AAV8 3' ITR |
| pAAV-2/rh.39-(eGFP) | AAV2 5' ITR | AAVrh.39 3' ITR |
| pAAV-8/2-(eGFP) | AAV8 5' ITR | AAV2 3' ITR |
| pAAV-8/8-(eGFP) | AAV8 5' ITR | AAV8 3' ITR |
| pAAV-8/rh.39-(eGFP) | AAV8 5' ITR | AAVrh.39 3' ITR |
| pAAV-rh.39/2-(eGFP) | AAVrh.39 5' ITR | AAV2 3' ITR |
| pAAV- rh.39/8-(eGFP) | AAVrh.39 5' ITR | AAV8 3' ITR |
| pAAV- rh.39/rh.39-(eGFP) | AAVrh.39 5' ITR | AAVrh.39 3' ITR |

Recombinant AAV (rAAV) particles (at a total concentration of $1\times10^{11}$ vector copies) comprising a nucleic acid construct of Table 1 and an AAV8 capsid protein (e.g., a capsid protein known to target liver, heart and muscle tissues) were systematically injected (via tail vein injection) into 8-week-old mice. The mice were euthanized four weeks after treatment with the rAAV particles and the liver, heart and muscle tissues were removed for testing.

Figure 2:
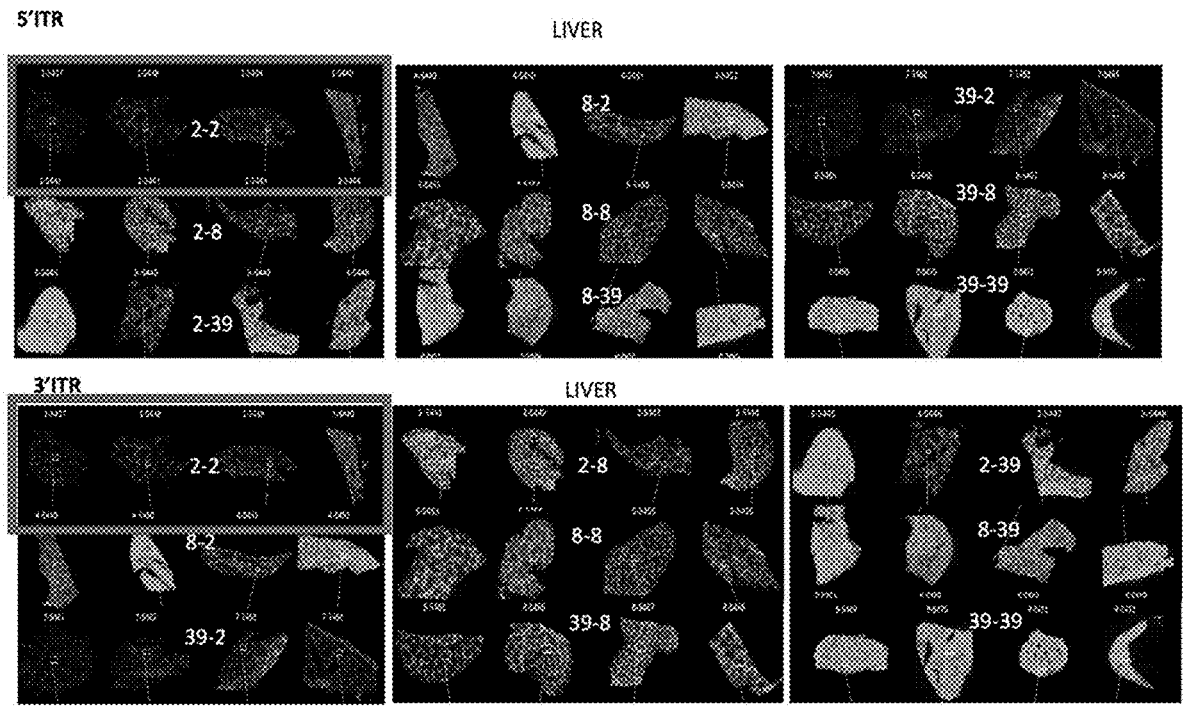
FIG. 2 depicts images of liver tissue from mice treated with rAAVs comprising hybrid ITR sequences of the disclosure.

The expression of eGFP in the liver, heart and muscle tissues of mice that were treated with rAAVs comprising the eGFP transgene were qualitatively assessed by fluorescence. As shown in FIG. 2, the hybrid AAV ITR constructs provided increased eGFP reporter expression based on fluorescence compared with the conventional AAV2-2 ITR combination. Notably, the hybrid AAV ITR constructs comprising an AAVrh.39 3' ITR provided significantly increased expression of eGFP. Similar fluorescence profiles were determined in the heart and muscle tissues of mice that were treated with rAAVs comprising the eGFP transgene.

Figure 3A:
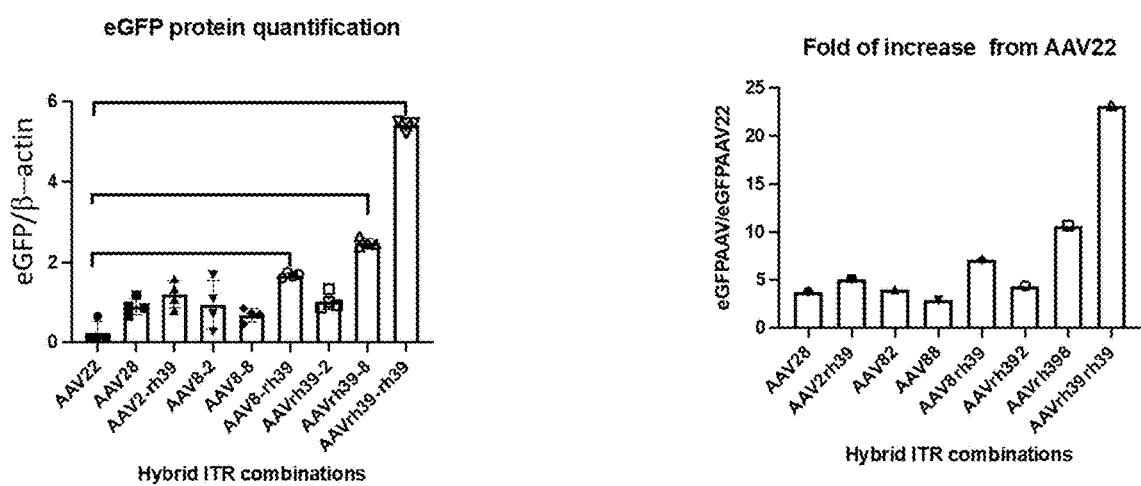
FIGS. 3A-3C depict graphs showing the ability of rAAVs comprising hybrid ITR sequences of the disclosure to provide in vivo transgene expression.
Figure 3B:
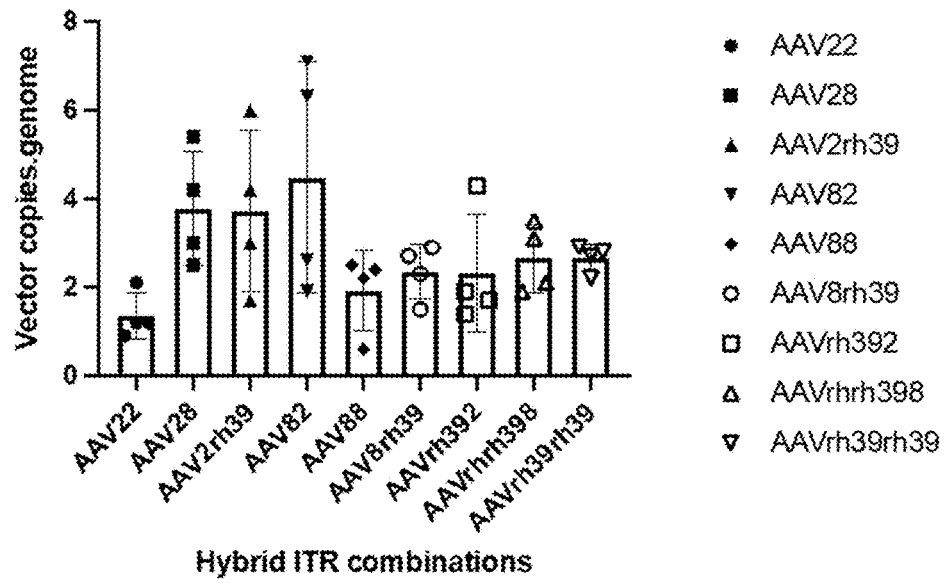

The concentration of eGFP protein expression in the liver was then determined by western blot analysis and normalized to a control protein (β-actin) (FIG. 3A). Mice treated with an rAAV comprising pAAV-2/2-(eGFP) had a very low concentration of eGFP relative to 0-actin in their liver tissues. Mice treated with an rAAV comprising a hybrid ITR construct, particularly a hybrid construct comprising an rh.39 ITR (e.g., pAAV-rh.39/8-(eGFP)) had elevated concentrations of eGFP relative to j-actin in their liver tissues compared to mice treated with the AAV2 ITR construct. Interestingly, none of the treated mice had elevated levels of vector copies of the rAAV particles relative to any other mice (FIG. 3B).

Figure 3C:
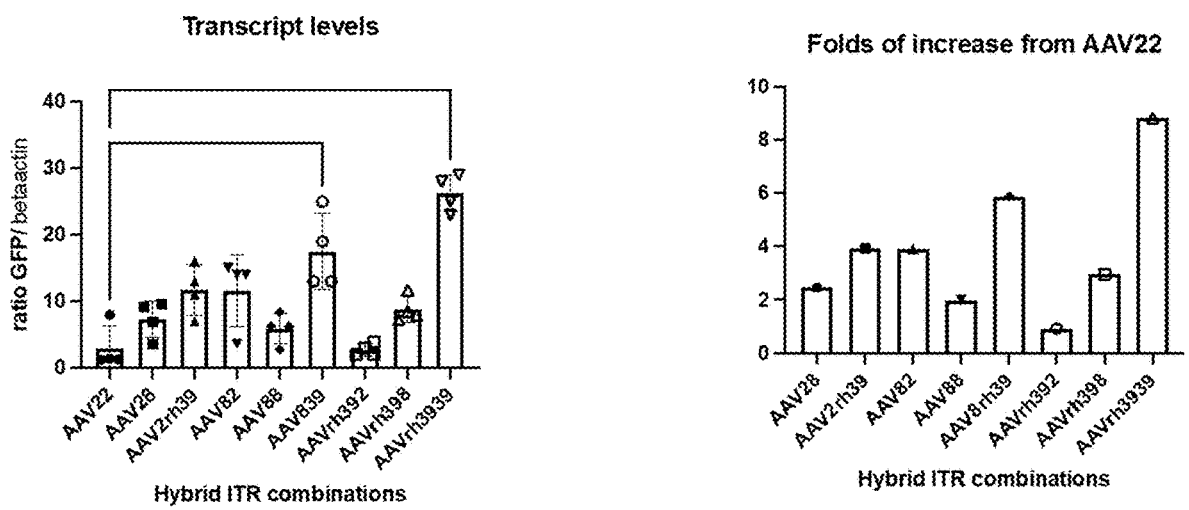
Figure 4A:
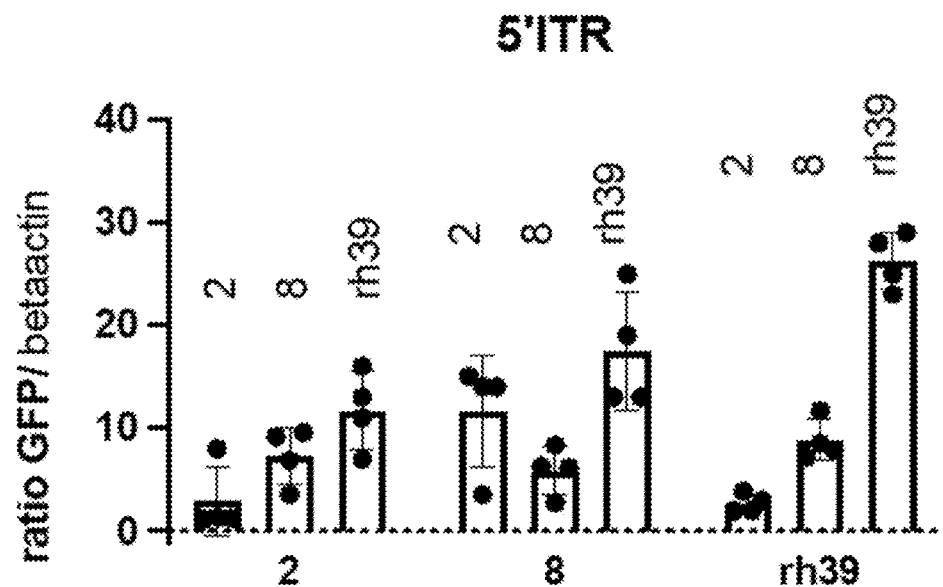
FIGS. 4A-4B depict graphs showing the impact of varying ITR sequences at the 5' end of a transgene and the 3' end of a transgene.
Figure 4B:
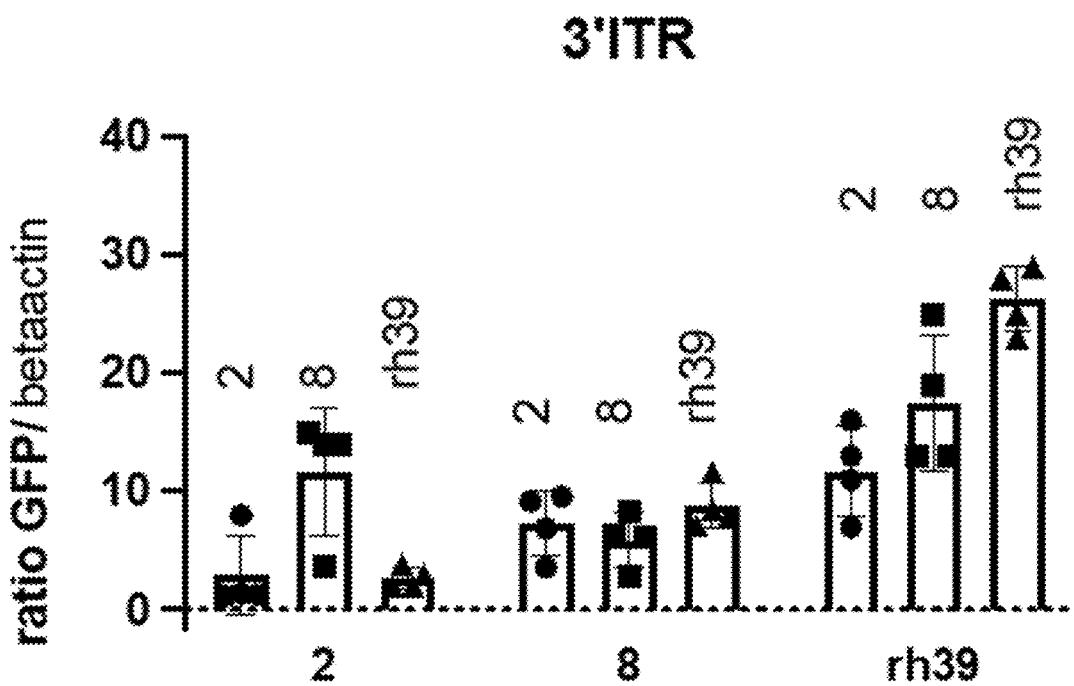

The concentration of eGFP transcript expression in the liver was then determined by ddPCR analysis and normalized to a control protein (β-actin) (FIG. 3C). The concentration of eGFP transcripts shared a similar profile with the observed eGFP protein levels. An analysis of the impact of varying 5' and 3' ITR sequences on the transgene expression was also determined using ddPCR data (FIGS. 4A-4B). It was found that inclusion of an AAVrh.39 3' ITR sequence had a more significant impact on transgene expression (see, FIG. 4B) compared to inclusion of an AAVrh.39 5' ITR sequence in a hybrid ITR construct.

TABLE 2

Nucleic acid constructs of Example 2 for expression of hA1AT

| Description | 5' ITR sequence | 3' ITR sequence |
| --- | --- | --- |
| pAAV-2/2-(hA1AT) | AAV2 5' ITR | AAV2 3' ITR |
| pAAV-2/8-(hA1AT) | AAV2 5' ITR | AAV8 3' ITR |
| pAAV-2/rh.39-(hA1AT) | AAV2 5' ITR | AAVrh.39 3' ITR |
| pAAV-8/2-(hA1AT) | AAV8 5' ITR | AAV2 3' ITR |
| pAAV-8/8-(hA1AT) | AAV8 5' ITR | AAV8 3' ITR |
| pAAV-8/rh.39-(hA1AT) | AAV8 5' ITR | AAVrh.39 3' ITR |
| pAAV-rh.39/2-(hA1AT) | AAVrh.39 5' ITR | AAV2 3' ITR |
| pAAV- rh.39/8-(hA1AT) | AAVrh.39 5' ITR | AAV8 3' ITR |
| pAAV- rh.39/rh.39-(hA1AT) | AAVrh.39 5' ITR | AAVrh.39 3' ITR |

Recombinant AAV (rAAV) particles (at a total concentration of $3\times10^{10}$ vector copies) comprising a nucleic acid construct of Table 2 and an AAV8 capsid protein (e.g., a capsid protein known to target liver, heart and muscle tissues) were systematically injected (via tail vein injection) into 8-week-old mice. Blood was drawn from the mice at weeks 1 and 3 following injection for analysis. The mice were euthanized four weeks after treatment with the rAAV particles and the liver, heart and muscle tissues were removed for testing.

Figure 5:
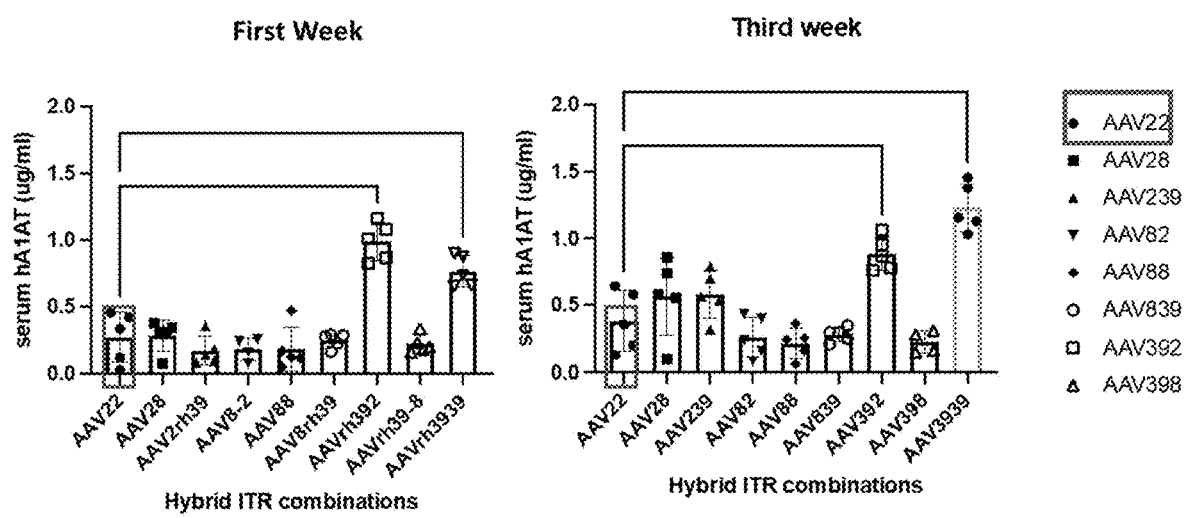
FIG. 5 depicts graphs showing the ability of rAAVs comprising hybrid ITR sequences of the disclosure to provide stable in vivo transgene expression for up to three weeks in serum of mice treated with rAAVs comprising hybrid ITR sequences of the disclosure.

The expression of hA1AT protein in the blood of mice that were treated with rAAVs comprising the hA1AT transgene were assessed by western blot analysis. As shown in FIG. 5, the hybrid AAV ITR constructs of the Example provided stable expression of hA1AT protein for up to three weeks after injection of the AAV particles. In particular, it was found that delivery of nucleic acid constructs that utilized rh.39 ITR sequences such as pAAV-rh.39/2-(hA1AT) (comprising an AAVrh.39 5' ITR) provided levels of serum hA1AT protein of up to 1.0 μg/mL.

Collectively, these data demonstrate that nucleic acid constructs comprising hybrid ITR sequences (such as those nucleic acid constructs comprising an AAV8 ITR and/or an AAVrh.39 ITR) are capable of providing stable in vivo transgene expression. Furthermore, these nucleic acid constructs are capable of providing stable and increased transgene expression, relative to nucleic acid constructs using conventional ITRs, without a significant increase in vector copy numbers. The nucleic acid constructs comprising hybrid ITR sequences of the disclosure provide novel and effective approaches for transgene delivery.

SEQUENCES

Novel AAV8 3' ITR (SEQ ID NO: 1)
ggttaccccctagtgatggagttggccactccctctatgcgcgctcgctcgctcggtggggccggcagagcagagactgccgtctgcgga
cctttggtccgcaggccccaccgagcgagcgagcgcgcatagagggagtggccaa Novel AAV8 5' ITR (SEQ ID NO: 2)
ttggccactccctctatgcgcgctcgctcgctcggtggggcctgcggaccaaaggtccgcagacggcagagactgactgccggcccc
accgagcgagcgagcgcgcatagagggagtggccaactccatcactaggggtaacc Novel AAVrh.39 3' ITR (SEQ ID NO: 3)
ggttaccccctagtgatggagttggccactccctctatgcgcgctcgctcgctcggtggggccggctgagcagagacagccgtctgcgga
cctttggtccgcaggccccaccgagcgagcgagcgcgcatagagggagtggccaa Novel AAVrh.39 5' ITR (SEQ ID NO: 4)
ttggccactccctctatgcgcgctcgctcgctcggtggggcctgcggaccaaaggtccgcagacggctgagactgacagccggcccc
accgagcgagcgagcgcgcatagagggagtggccaactccatcactaggggtaacc Novel AAV8 genome (SEQ ID NO: 5)
ttggccactccctctatgcgcgctcgctcgctcggtggggcctgcggaccaaaggtccgcagacggcagagactgactgccggcccc
accgagcgagcgagcgcgcatagagggagtggccaactccatcactaggggtaacctcccacgctgccgcgtcagcgctgacgtaaat
tacgtcataggggagtggtcctgtattagctgtcacgtgagtgttttgcggcattttgaggtcatttgaggtatatatggccg
agtgagcgagcaggatctccattttgaccgcgaaatttgaacgagcagcagccatgccgggcttctacgagatcgtgatcaaggtgccga
gcgacctggacgagcacctgccgggcatttctgactcgtttgtgaactgggtggccgagaaggaatgggagctgccccccggattctgaca
tggatcggaatctgatcgagcaggcaccctgaccgtggccgagaagctgcagcgcgacttcctggtccaatggcgccgcgtgagtaag
gccccggagccctcttctttgttcagttcgagaagggcgagagctactttcacctgcacgttctggtcgagaccacggggtcaagtccat
ggtgctaggccgcttcctgagtcagattcgggagaagctgctccagaccatctaccgcggggtcgagcccacgctgcccaactggttcgc
ggtgaccaagacgcgtaatggcgccggcggggggaacaaggtggtggacgagtgctacatccccaactacctcctgcccaagactcag
cccgagctgcagtgggcgtggactaacatggaggagtatataagcgcgtgcttgaacctggccgagcgcaaacggctcgtggcgcagc
acctgacccacgtcagccagacgcaggagcaggaacaaggagaatctgaaccccaattctgacgcccgtgatcaggtcaaaaacctcc
gcgcgctatatggagctggtcgggtggctggtggtggaccgggggcatcacctccgagaagcagtggatccaggaggaccaggcctcgtaca
tctccttcaacgccgcctccaactcgcggtcccagatcaaggccgcgctggacaatgccggcaagatcatggcgctgaccaaatccgcg
cccgactacctggtggggccctcgctgcccgcggacattacccagaaccgcatctaccgcatcctcgctctcaacggctacgaccctgcc
tacgccggctccgtctttctcggctgggctcagaaaaagttcgggaaacgcaacaccatctggctgtttggacccgccaccaccggcaag
accaacattgcggaagccatcgcccacgccgtgccctttcacggctgcgtcaactggaccaatgagaacttccctcaatgattgcgtcga
caagatggtgatctggtgggaggagggcaagatgacggccaaggtcgtggagtccgccaaggccattctcggcggcagcaaggtgcg
cgtgaccaaaagtgcaagtcgtccgcccagatcgaccccacccccgtgatcgtcacctccaacaccaacatgtgcgccgtgattgacgg
gaacagcaccaccttcgagcaccagcagcctctccaggaccggatgtttaagttcgaactcacccgccgtctggagcacgactttggcaa
ggtgacaaagcaggaagtcaaagagttcttccgctgggcccagtgatcacggtgaccgaggtggcgcatgagttttacgtcagaaagggcg
gagccagcaaaagacccgccccgatgacgcggataaaagcgagcccaagcgggcctgccctcagtcgcggatccatcgacgtcag
acgcggaaggagctccggtggactttgccgacaggtaccaaaacaaatgttctcgtcacgcgggcatgcttcagatgctgtttccctgcaa
aacgtgcgagagaatgaatcagaatttcaacatttgcttcacacacggggtcagagactgctcagagtgttcccggcgtgtcagaatctc
aacggtcgtcagaaagaggacgtatcggaaactctgtgcgattcatcatctgctgggcgcccctcccgagattgcttgctgctcggcctgcga
tctggtcaacgtggacctggatgactgtgtttctgagcaataaatgacttaaaccaggtatggctgccgatggttatcttccagattggctcga
ggacaacctctctgagggcattcgcgagtggtgggcgctgaaacctggagccccgaagcccaaagccaaccagcaaaagcaggacga
cggccggggtctggtgcttcctggctacaagtacctcggaccccttcaacggactcgacaaggggggagcccgtcaacgcggcggacgca
gcggccctcgagcacgacaaggcctacgaccagcagctgcaggcggggtgaacatccgtacctgcgggtataaccacgccgagccgag
tttcaggagcgtctgcaagaagatacgtcttttgggggcaacctcggggcgagcagtcttccaggccaagaagcgggttctcgaacctctcg
gtctggttgaggaaggcgctaagacggctcctggaaaagaagaccggtagagccatcacccccagcgttctccagactcctctacgggc
atcggcaagaaaggccaacagcccgccagaaaagactcaattttggtcagactggcgactcagagtcagttccagaccctcaacctctc
ggagaacctccagcagcgccctctggtgtgggacctaataacaatggcggcgggtggcgccaccaatggcgagacaataacgaaggcg
ccgacggagtgggtagttcctcgggaaatttggcattgcgattccacatggctgggcgacagagtcatcaccaccgcacccgaacctgg
gccctgccccactacaacaaccacctctacaagcaaatctccaacgggacatcgggaggagccaccaacgacaacacctacttcggcta
cagcaccccctgggggtattttgactttaacagattccactgccacttttcaccacgtgactggcagcgactcatcaacaacaactggggatt
ccggcccaagagactcagcttcaagctcttcaacatccaggtcaaggaggtcacgcagaatgaaggccaccaacatccgccaataacc
tcaccagcaccatccaggtgtttacggactcggagtaccagctgccgtacgtcctcggctctgcccaccagggctgcctcctgttcccg
gcggacgtgttcatgattcccccagtacggctacctaacactcaacaacggtagtcaggccgtgggacgctcctcctttctactgcctggaata
cttccttcgcagatgctgagaaccggcaacaacttccagtttacttacacccttgagggacgtgcctttccacagcagctacgcccacagcca
gagcttggaccggctgatgaatcctctgattgaccagtacctgtactacttgtctcggactcaaacaacaggaggcacggcaaatacgcag
actctgggcttcagccaaggtgggcctaatacaatggccaatcaggcaaaggctgtgtctctgaaccccgccaataggcagacaaacgcgtc
tcaacgacaaccgggcaaaacaacaatagcaactttgcctggactgctgggaccaaataccatcgaatggaagaaattcattggctaatc
ctggcatcgctatggcaacacaaaagacgacaaggagcgtttttttcccagtaacgggatcctgattttttggcaaacaaatgctgccaga
gacaatgcggattacagcgatgtcatgctcaccagcgaggaagaaatcaaaaccactaaccctgtggctacagaggaatacggtatcgtg
gcagataacttgcagcagcaaaacacggctcctcaaatttggaacctgtcaacaccaggggcttaccccggtatggtctgcagagaaccg
ggacgtgtacctgcagggtcccatctgggccaagattcctcacacggacggcaacttccaccccctctccgctgatgggcggctttggcctg
aaacatcctccgcctcagatcctgatcaagaacacgcctgtacctgcggatcctccgaccaccttcaaccagtcaaagctgaactctttcatc
acgcaatacagcaccggacaggtcagcgtggaattgaatgggagctgcagaaggaaaacagcaagcgctggaaccccgagatccag
tacacctccaactactacaaatctacaagtgtggccttgctgttaataacaaggcgtgtactctgaacccgccccattggcacccgttacc
tcaccccgtaatctgtaattgcctgttaatcaataaaccggttgattcgtttcagttgaacttttggcctactgtccttcttatcttatctcgtctccatgg
caactggttaaacattaactGCTTGGGTGCGCTTCGCGATAAGGGACTGACGTCATCggttaccccctag
tgatggagttggccactccctctatgcgcgctcgctcgctcggtggggccggcagagcagagctctgccgtctgcgggaccttttggtccgca
ggccccaccgagcgagcgagcgcgcatagagggagtggccaa Novel AAVrh.39 genome (SEQ ID NO: 6)
ttggccactccctctatgcgcgctcgctcgctcggtggggcctgcggaccaaaggtccgcagacggctgagtctgtctcagccggcccc
accgagcgagcgagcgcgcatagagggagtggccaactccatcactaggggtaaccGCGAAGCGCTCCCACGCTG
CCGCGTcagcgctgacgtaaatcacgtcataggggagtggtcctgtattagctgtcacgtgagtgcttttgcgacagtttgcgacacca
cgtggtcacaggggtatatatggccgagtgagcacgcaggatctccattttgagcgcgaatttgaacgagcagcagccatgccgggct
tctacgagatcgtgatcaaggtgccgagcgacctggacgagcacctgccgggcatttctgactcgttcgtgaactgggtggccgagaagg
aatgggagctgccccggattctgacatggatcggaatctgatcgagcaggcaccctgaccgtggccgagaagctgcagcgcgacttc
ctggtcgaatggcgccgcgtgagtaaggccccggaggcctcttctttgttcagttcgagaagggggaaagctactttcacctgcacgttct ggtcgagaccacggggtcaagtccatggtgctgggccgcttcctgagccagattcgcgaaaagctcgtgcaacgcatctaccgcgggg
tcgagcccacgctgcccaactggttcgcggtgaccaagacgcgaaatggcgccggcgggggaacaaggtggtggacgagtgctaca
tccccaactacctcctgcccaagacgcagcccgagctgcagtgggcgtggactaacatgggagtatataagcgcgtgtctgaacctcg
cggagcgtaaacggctcgtggcgcagcacctgacccacgtcagccagacgcaggagcagaacaaggagaatctgaacccgaattctg
acgcgcccgtgatcaggtcaaaaacctccgcgcgctacatggagctggtcgggtggctggtggaccggggcatcacctccgagaagca
gtggatccaggaggaccaggcctcgtacatctccttcaacgccgcctccaactcgcggtcccagatcaaggccgcgctggacaatgccg
gaaagatcatggcgctgaccaaatccgcgcccgactacctggtgggccgtccttacccgcggacattaaggccaaccgcatctaccgc
atcctggagctcaacggctacgaccccgcctacgccggctccgtcttcctgggctgggcgcagaaaaagttcggtaaacgcaacaccatc
tggctcttcgggccgccaccaccggcaagaccaacatcgcggaagccatcgcccacgccgtgcccttctacggctgcgtcaactggac
caatgagaactttcccttcaacgattgcgtcgacaagatggtgatctggtggaggagggcaagatgaccgccaaggtcgtggagtccgc
caaggccattctgggtggaagcaaggtgcgcgtgaccaaaagtgcaagtcatcggcccagatcgaccccacgcccgtgatcgtcacct
ccaacaccaacatgtgcgccgtgatcgacgggaacagcaccaccttcgagcaccagcagcccctgcaggaccgcatgttcaagttcgag
ctcacccgccgtctggagcacgactttggcaaggtgaccaagcaggaagtcaaagagttcttccgctgggctcaggatcacgtgactgag
gtggcgcatgagttctacgtcagaaagggcggagccaccaaaagacccgcccccagtgacgcggatataagcgagcccaagcgggcc
tgcccctcagttgcggagccatcgacgtcagacgcggaagcaccggtggactttgcggacaggtaccaaaacaaatgttctcgtcacgcg
ggcatgcttcagatgctgtttccctgcaagacatgcgagagaatgaatcagaatttcaacgtctgcttcacgcacggggtcagggacgctc
agagtgcttccccggcgcgtcagaatctcaaccctgtcgtcagaaaaaagacgtatcagaaactgtgcgcgattcatcatctgctgggcgg
gcacccgagattgcgtgttcggcctgcgatctcgtcaacgtggacttggatgactgtgtttctgagcaataaatgacttaaaccaggtatggc
tgctgacggttatcttccagattggctcgaggacaacctctctgagggcattcgcgagtggtgggacctgaaacctggagcccccaagccc
aaggccaaccagcgaagcaggacgacggccgggtctggtgcttcctcgagactacctcggaccctcaacggactcgacaagg
gggagcccgtcaacgcggcggacgcagcggccctcgagcacgcacaaggcctacgaccagcgctcaaagcgggtgacaatccgtac
ctgccggtataaccacgccgacgccgagtttcaggagcgtctgcaagaagatacgtcttttgggggcaacctcgggcgagcagtcttccag
gccaagaagcgggttctcgaacctctcggtctggttgaggaagctgctaagacggctcctggaaagaagagaccggtagaaccgtcacc
tcagcgttccccgactcctccacgggcatcggcaagaaaggccagcagcccgctaaaaaggagactgaactttggtcagactggcgact
cagagtcagtccccgaccctcaaccaatcggagaaccaccagcaggcccctctggtctgggatctggtacaatggctgcaggcggtggc
gctccaatggcagacaataacgaaggcgccgacgagtgggtagttcctcaggaaattggcattgcgattccacatggctgggcgacag
agtcatcaccaccagcacccgaacctgggccctgcccacctacaacaaccacctctacaagcaaatatccAATGGGACATCG
GGAGGAAGCACCAACGACAACACCTACTTCGGCTACAGCACCCCCTGGGGGTATTT
TGACTTCAACAGATTCCACTGCCACTTCTCACCACGTGACTGGCAGCGACTCATCAA
CAACAACTGGGGATTCCGGCCAAAAAGACTCAGCTTCAAGCTCTTCAACATCCAGG
TCAAGGAGGTCACGCAGAATGAAGGCACCAAGACCATCGCCAATAACCTTACCAGC
ACGATTCAGGTATTTACGGACTCGGAATACCAGCTGCCGTACGTCCTCGGCTCCGCG
CACCAGGGCTGCCTGCCTCCGTTCCCGGCGGACGTCTTCATGattcccccagtacggctaccttacac
tgaacaatggaagtcaagccgtaggccgttcctccttctactgcctggaatattttccatctcaaatgctgcgaactggaaacaattttgaattc
agctacaccttcgaggacgtgcctttccacagcagctacgcacacagccagagcttggaccgactgatgaatcctctcatcgaccagtacc
tgtactacttatccagaactcagtccacaggaggaacctcaaggtacccagccaattgttatttttctcaagctgggcctgcaaacatgtcggctca
ggctaagaactggctacctggacctgtaccggcagcagcgagtctctacgacactgtgcaaaacaacaacagcaactttgcttggact
ggtgccaccaaaatatcacctgaacggaagagactctttggtaaatcccggtgtcgccatgcaactccacaaggacgacgaggaacgcttc
ttcccgtcgagtggagtcctgatgtttggaaaacagggtgctggaagagacaatgtggactacagcagcgttatgctaaccagcgaagaa
gaaattaaaaccactaaccctgtagccacagaacaatacggtgtggtggctgacaacttgcagcaaaccaatacagggcctattgtgggaa
atgtcaacagccaaggagccttacctggcatggtctggcagaaccggaacgtgtacctgcagggtcccatctgggcaagattcctcaca
cggacggcaacttccaccttcaccgctaatgggaggattggactgaagcaccacctcctcagatcctgatcaagaacacgccggtac
ctgccggatcctccaacaacgttcagccaggcgaaattggcttccttcattacgcagtacagcaccggacaggtcagcgtggaaatcgagtg
ggagctgcagaaggagaacagcaaacgctggaacccagagattcagtacacttcaaactactacaaatctacaaatgtggactttgctgtc
aatacagagggaacttattctgagcctcgcccccattggtactcgttacctcacccgtaatctgtaattgctaattcatcaataaaacgtttgatc
gtttcagttgaactttggtctccgtgtgcttcttatcttatctcgtctccatggcaactggttacacattaactgcttggtgcgcttcgcGATCA
TAAATGACTTACGTCATCGggttaccccctagtgatgagttggccactccctctatgcgcgctcgctcgctcggtgggc
cggctgagcagagctcagccgtctgcggacctttggtccgcaggccccaccgagcgagcgagcgcgcatagagggagtggccaa Novel AAV8 Rep78 protein (SEQ ID NO: 7)
MPGFYEIVIKVPSDLDEHLPGISDSFVNWVAEKEWELPPDSDMDRNLIEQAPLTVAEKL
QRDFLVQWRRVSKAPEALFFVQFEKGESYFHLHVLVETTGVKSMVLGRFLSQIREKLV
QTIYRGVEPTLPNWFAVTKTRNGAGGGNKVVDECYIPNYLLPKTQPELQWAWTNMEE
YISACLNLAERKRLVAQHLTHVSQTQEQNKENLNPNSDAPVIRSKTSARYMELVGWLV
DRGITSEKQWIQEDQASYISFNAASNSRSQIKAALDNAGKIMALTKSAPDYLVGPSLPAD
ITQNRIYRILALNGYDPAYAGSVFLGWAQKKFGKRNTIWLFGPATTGKTNIAEAIAHAV
PFYGCVNWTNENFPFNDCVDKMVIWWEEGKMTAKVVESAKAILGGSKVRVDQKCKS
SAQIDPTPVIVTSNTNMCAVIDGNSTTFEHQQPLQDRMFKFELTRRLEHDFGKVTKQEV
KEFFRWASDHVTEVAHEFYVRKGGASKRPAPDDADKSEPKRACPSVADPSTSDAEGAP
VDFADRYQNKCSRHAGMLQMLFPCKTCERMNQNFNICFTHGVRDCSECFPGVSESQPV
VRKRTYRKLCAIHHLLGRAPEIACSACDLVNVDLDDCVSEQ*

Novel AAV8 Rep68 protein (SEQ ID NO: 8)
MPGFYEIVIKVPSDLDEHLPGISDSFVNWVAEKEWELPPDSDMDRNLIEQAPLTVAEKL
QRDFLVQWRRVSKAPEALFFVQFEKGESYFHLHVLVETTGVKSMVLGRFLSQIREKLV
QTIYRGVEPTLPNWFAVTKTRNGAGGGNKVVDECYIPNYLLPKTQPELQWAWTNMEE
YISACLNLAERKRLVAQHLTHVSQTQEQNKENLNPNSDAPVIRSKTSARYMELVGWLV
DRGITSEKQWIQEDQASYISFNAASNSRSQIKAALDNAGKIMALTKSAPDYLVGPSLPAD
ITQNRIYRILALNGYDPAYAGSVFLGWAQKKFGKRNTIWLFGPATTGKTNIAEAIAHAV
PFYGCVNWTNENFPFNDCVDKMVIWWEEGKMTAKVVESAKAILGGSKVRVDQKCKS
SAQIDPTPVIVTSNTNMCAVIDGNSTTFEHQQPLQDRMFKFELTRRLEHDFGKVTKQEV
KEFFRWASDHVTEVAHEFYVRKGGASKRPAPDDADKSEPKRACPSVADPSTSDAEGAP
VDFADRLARGHSL*

Novel AAV8 Rep52 protein (SEQ ID NO: 9)
MELVGWLVDRGITSEKQWIQEDQASYISFNAASNSRSQIKAALDNAGKIMALTKSAPD
YLVGPSLPADITQNRIYRILALNGYDPAYAGSVFLGWAQKKFGKRNTIWLFGPATTGKT

| SEQUENCES |
|---|
| NIAEAIAHAVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFKFELTRRLEHD<br>FGKVTKQEVKEFFRWASDHVTEVAHEFYVRKGGASKRPAPDDADKSEPKRACPSVAD<br>PSTSDAEGAPVDFADRYQNKCSRHAGMLQMLFPCKTCERMNQNFNICFTHGVRDCSEC<br>FPGVSESQPVVRKRTYRKLCAIHHLLGRAPEIACSACDLVNVDLDDCVSEQ* |
| Novel AAV8 Rep40 protein (SEQ ID NO: 10)<br>MELVGWLVDRGITSEKQWIQEDQASYISFNAASNSRSQIKAALDNAGKIMALTKSAPD<br>YLVGPSLPADITQNRIYRILALNGYDPAYAGSVFLGWAQKKFGKRNTIWLFGPATTGKT<br>NIAEAIAHAVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFKFELTRRLEHD<br>FGKVTKQEVKEFFRWASDHVTEVAHEFYVRKGGASKRPAPDDADKSEPKRACPSVAD<br>PSTSDAEGAPVDFADRLARGHSL* |
| Novel AAVrh.39 Rep78 protein (SEQ ID NO: 11)<br>MPGFYEIVIKVPSDLDEHLPGISDSFVNWVAEKEWELPPDSDMDRNLIEQAPLTVAEKL<br>QRDFLVEWRRVSKAPEALFFVQFEKGESYFHLHVLVETTGVKSMVLGRFLSQIREKLV<br>QRIYRGVEPTLPNWFAVTKTRNGAGGGNKVVDECYIPNYLLPKTQPELQWAWTNMEE<br>YISACLNLAERKRLVAQHLTHVSQTQEQNKENLNPNSDAPVIRSKTSARYMELVGWLV<br>DRGITSEKQWIQEDQASYISFNAASNSRSQIKAALDNAGKIMALTKSAPDYLVGPSLPAD<br>IKANRIYRILELNGYDPAYAGSVFLGWAQKKFGKRNTIWLFGPATTGKTNIAEAIAHAV<br>PFYGCVNWTNENFPFNDCVDKMVIWWEEGKMTAKVVESAKAILGGSKVRVDQKCKS<br>SAQIDPTPVIVTSNTNMCAVIDGNSTTFEHQQPLQDRMFKFELTRRLEHDFGKVTKQEV<br>KEFFRWAQDHVTEVAHEFYVRKGGATKRPAPSDADISEPKRACPSVAEPSTSDAEAPV<br>DFADRYQNKCSRHAGMLQMLFPCKTCERMNQNFNVCFTHGVRDCSECFPGASESQPV<br>VRKKTYQKLCAIHHLLGRAPEIACSACDLVNVDLDDCVSEQ* |
| Novel AAVrh.39 Rep68 protein (SEQ ID NO: 12)<br>MPGFYEIVIKVPSDLDEHLPGISDSFVNWVAEKEWELPPDSDMDRNLIEQAPLTVAEKL<br>QRDFLVEWRRVSKAPEALFFVQFEKGESYFHLHVLVETTGVKSMVLGRFLSQIREKLV<br>QRIYRGVEPTLPNWFAVTKTRNGAGGGNKVVDECYIPNYLLPKTQPELQWAWTNMEE<br>YISACLNLAERKRLVAQHLTHVSQTQEQNKENLNPNSDAPVIRSKTSARYMELVGWLV<br>DRGITSEKQWIQEDQASYISFNAASNSRSQIKAALDNAGKIMALTKSAPDYLVGPSLPAD<br>IKANRIYRILELNGYDPAYAGSVFLGWAQKKFGKRNTIWLFGPATTGKTNIAEAIAHAV<br>PFYGCVNWTNENFPFNDCVDKMVIWWEEGKMTAKVVESAKAILGGSKVRVDQKCKS<br>SAQIDPTPVIVTSNTNMCAVIDGNSTTFEHQQPLQDRMFKFELTRRLEHDFGKVTKQEV<br>KEFFRWAQDHVTEVAHEFYVRKGGATKRPAPSDADISEPKRACPSVAEPSTSDAEAPV<br>DFADRLARGHSL* |
| Novel AAVrh.39 Rep52 protein (SEQ ID NO: 13)<br>MELVGWLVDRGITSEKQWIQEDQASYISFNAASNSRSQIKAALDNAGKIMALTKSAPD<br>YLVGPSLPADIKANRIYRILELNGYDPAYAGSVFLGWAQKKFGKRNTIWLFGPATTGKT<br>NIAEAIAHAVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFKFELTRRLEHD<br>FGKVTKQEVKEFFRWAQDHVTEVAHEFYVRKGGATKRPAPSDADISEPKRACPSVAEP<br>STSDAEAPVDFADRYQNKCSRHAGMLQMLFPCKTCERMNQNFNVCFTHGVRDCSECF<br>PGASESQPVVRKKTYQKLCAIHHLLGRAPEIACSACDLVNVDLDDCVSEQ* |
| Novel AAVrh.39 Rep40 protein (SEQ ID NO: 14)<br>MELVGWLVDRGITSEKQWIQEDQASYISFNAASNSRSQIKAALDNAGKIMALTKSAPD<br>YLVGPSLPADIKANRIYRILELNGYDPAYAGSVFLGWAQKKFGKRNTIWLFGPATTGKT<br>NIAEAIAHAVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFKFELTRRLEHD<br>FGKVTKQEVKEFFRWAQDHVTEVAHEFYVRKGGATKRPAPSDADISEPKRACPSVAEP<br>STSDAEAPVDFADRLARGHSL* |
| Novel AAV8 cap protein (SEQ ID NO: 15)<br>MAADGYLPDWLEDNLSEGIREWWALKPGAPKPKANQQKQDDGRGLVLPGYKYLGPF<br>NGLDKGEPVNAADAAALEHDKAYDQQLQAGDNPYLRYNHADAEFQERLQEDTSFGG<br>NLGRAVFQAKKRVLEPLGLVEEGAKTAPGKKRPVEPSPQRSPDSSTGIGKKGQQPARKR<br>LNFGQTGDSESVPDPQPLGEPPAAPSGVGPNTMAAGGGAPMADNNEGADGVGSSSGN<br>WHCDSTWLGDRVITTSTRTWALPTYNNHLYKQISNGTSGGATNDNTYFGYSTPWGYF<br>DFNRFHCHFSPRDWQRLINNNWGFRPKRLSFKLFNIQVKEVTQNEGTKTIANNLTSTIQ<br>VFTDSEYQLPYVLGSAHQGCLPPFPADVFMIPQYGYLTLNNGSQAVGRSSFYCLEYFPS<br>QMLRTGNNFQFTYTFEDVPFHSSYAHSQSLDRLMNPLIDQYLYYLSRTQTTGGTANTQT<br>LGFSQGGPNTMANQAKNWLPGPCYRQQRVSTTTGQNNNSNFAWTAGTKYHLNGRNS<br>LANPGIAMATHKDDKERFFPSNGILIFGKQNAARDNADYSDVMLTSEEEIKTTNPVATE<br>EYGIVADNLQQQNTAPQIGTVNSQGALPGMVWQNRDVYLQGPIWAKIPHTDGNFHPSP<br>LMGGFGLKHPPPQILIKNTPVPADPPTTFNQSKLNSFITQYSTGQVSVEIEWELQKENSKR<br>WNPEIQYTSNYYKSTSVDFAVNTEGVYSEPRPIGTRYLTRNL* |
| Novel AAVrh.39 cap protein (SEQ ID NO: 16)<br>MAADGYLPDWLEDNLSEGIREWWDLKPGAPKPKANQQKQDDGRGLVLPGYKYLGPF<br>NGLDKGEPVNAADAAALEHDKAYDQQLKAGDNPYLRYNHADAEFQERLQEDTSFGG<br>NLGRAVFQAKKRVLEPLGLVEEAAKTAPGKKRPVEPSPQRSPDSSTGIGKKGQQPAKK<br>RLNFGQTGDSESVPDPQPIGEPPAGPSGLGSGTMAAGGGAPMADNNEGADGVGSSSGN<br>WHCDSTWLGDRVITTSTRTWALPTYNNHLYKQISNGTSGGSTNDNTYFGYSTPWGYFD |

| SEQUENCES |
|---|
| FNRFHCHFSPRDWQRLINNNWGFRPKRLSFKLFNIQVKEVTQNEGTKTIANNLTSTIQVF
TDSEYQLPYVLGSAHQGCLPPFPADVFMIPQYGYLTLNNGSQAVGRSSFYCLEYFPSQM
LRTGNNFEFSYTFEDVPFHSSYAHSQSLDRLMNPLIDQYLYYLSRTQSTGGTQGTQQLL
FSQAGPANMSAQAKNWLPGPCYRQQRVSTTLSQNNNSNFAWTGATKYHLNGRDSLV
NPGVAMATHKDDEERFFPSSGVLMFGKQGAGRDNVDYSSVMLTSEEEIKTTNPVATEQ
YGVVADNLQQTNTGPIVGNVNSQGALPGMVWQNRDVYLQGPIWAKIPHTDGNFHPSP
LMGGFGLKHPPPQILIKNTPVADPPTTFSQAKLASFITQYSTGQVSVEIEWELQKENSKR
WNPEIQYTSNYYKSTNVDFAVNTEGTYSEPRPIGTRYLTRNL*

AAV2 ITR nucleic acid sequence (SEQ ID NO: 17)
ttggccactccctctctgcgcgctcgctcgctcactgaggccgcccgggcaaagcccgggcgtcgggcgacctttggtcgcccggcctc
agtgagcgagcgagcgcgcagagagggagtggccaactccatcactaggggttcct |

What is claimed is:

1. A recombinant adeno-associated viral (rAAV) vector comprising a transgene flanked by inverted terminal repeats (ITRs), wherein a first ITR is an AAV8 ITR and a second ITR is an AAVrh.39 ITR, and wherein
   (a) the first ITR comprises the entirety of the nucleic acid sequence of SEQ ID NOs: 1 or 2; and/or
   (b) the second ITR comprises the entirety of the nucleic acid sequence of SEQ ID NOs: 3 or 4.

2. The rAAV vector of claim 1, wherein:
   (a) the first ITR is an AAV8 5' ITR and the second ITR is an AAVrh.39 3' ITR; or
   (b) the first ITR is an AAV8 3' ITR and the second ITR is an AAVrh.39 5' ITR.

3. The rAAV vector of claim 1, wherein the first ITR consists of the nucleic acid sequence of SEQ ID NO: 2.

4. The rAAV vector of claim 1, wherein the second ITR consists of the nucleic acid sequence of SEQ ID NO: 3.

5. The rAAV vector of claim 1, wherein the first ITR consists of the nucleic acid sequence of SEQ ID NO: 1.

6. The rAAV vector of claim 1, wherein the second ITR consists of the nucleic acid sequence of SEQ ID NO: 4.

7. A host cell comprising the rAAV vector of claim 1.

8. The host cell of claim 7, further comprising a Rep protein having the amino acid sequence set forth in any one of SEQ ID NOs: 7-14 and/or a Cap protein having the amino acid sequence set forth in any one of SEQ ID NO: 15 or 16.

9. The host cell of claim 7, wherein the cell is a HEK293 cell or is derived from a HEK293 cell.

10. A pseudotyped adeno-associated virus (AAV comprising
    (i) inverted terminal repeats (ITRs) comprising:
       (a) an AAV8 3' ITR comprising SEQ ID NO: 1 and an AAV8 5' ITR comprising SEQ ID NO: 2;
       (b) an AAV8 3' ITR comprising SEQ ID NO: 1 and an AAVrh39 5' ITR comprising SEQ ID NO: 4; or
       (c) an AAV8 5' ITR comprising SEQ ID NO: 2 and an AAVrh39 3' ITR comprising SEQ ID NO: 3; and
    (ii) a capsid protein of a non-AAV8 AAV serotype.

11. The pseudotyped AAV of claim 10, comprising an AAV8 3' ITR comprising SEQ ID NO: 1 and an AAV8 5' ITR comprising SEQ ID NO: 2.

12. A pseudotyped AAV comprising
    (i) inverted terminal repeats (ITRs) comprising
       (a) an AAVrh.39 5' ITR comprising SEQ ID NO: 4 and an AAVrh.39 3' ITR comprising SEQ ID NO: 3;
       (b) an AAVrh.39 5' ITR comprising SEQ ID NO: 4 and an AAV8 3' ITR comprising SEQ ID NO: 1; or
       (c) an AAVrh.39 3' ITR comprising SEQ ID NO: 3 and an AAV8 5' ITR comprising SEQ ID NO: 2; and
    (ii) a capsid protein of a non-AAVrh.39 AAV serotype.

13. The pseudotyped AAV of claim 12, comprising an AAVrh.39 5' ITR comprising SEQ ID NO: 4 and an AAVrh.39 3' ITR comprising SEQ ID NO: 3.

14. The pseudotyped AAV of claim 10, wherein the non-AAV8 AAV serotype is AAV1, AAV2, AAV3B, AAV9, AAVrh.8, AAVrh.10, or AAVrh.39.

15. The pseudotyped AAV of claim 12, wherein the non-AAVrh.39 AAV serotype is AAV1, AAV2, AAV3B, AAV8, AAV9, AAVrh.8, or AAVrh.10.

16. A recombinant adeno-associated viral (rAAV) vector comprising a transgene flanked by inverted terminal repeats (ITRs), wherein a first ITR is an AAV2 ITR and a second ITR is an AAVrh.39 ITR or an AAV8 ITR, and wherein the second ITR comprises the entirety of the nucleic acid sequence of any one of SEQ ID NOs: 1-4.

17. The rAAV vector of claim 16, wherein the first ITR comprises the nucleic acid sequence set forth in SEQ ID NO: 17.

18. The rAAV vector of claim 16, wherein the second ITR consists of the nucleic acid sequence set forth in any one of SEQ ID NOs: 1-4.

19. A recombinant adeno-associated virus (rAAV) comprising:
   (i) the rAAV vector of claim 1; and
   (ii) an AAV capsid protein, optionally wherein the AAV capsid protein is not of the same serotype as any of the ITRs of the rAAV.

20. A method for delivering a transgene to a cell or subject, the method comprising administering to the cell or subject the rAAV of claim 19.

21. The pseudotyped AAV of claim 10, comprising an AAV8 3' ITR comprising SEQ ID NO: 1 and an AAVrh.39 5' ITR comprising SEQ ID NO: 4.

22. The pseudotyped AAV of claim 10, comprising an AAV8 5' ITR comprising SEQ ID NO: 2 and an AAVrh.39 3' ITR comprising SEQ ID NO: 3.

23. The pseudotyped AAV of claim 12, comprising an AAVrh.39 5' ITR comprising SEQ ID NO: 4 and an AAV8 3' ITR comprising SEQ ID NO: 1.

24. The pseudotyped AAV of claim 12, comprising an AAVrh.39 3' ITR comprising SEQ ID NO: 3 and an AAV8 5' ITR comprising SEQ ID NO: 2.

\* \* \* \* \*